US010965933B2

(12) United States Patent
Jarc

(10) Patent No.: US 10,965,933 B2
(45) Date of Patent: *Mar. 30, 2021

(54) MEDICAL DEVICES, SYSTEMS, AND METHODS USING EYE GAZE TRACKING FOR STEREO VIEWER

(71) Applicant: INTUITIVE SURGICAL OPERATIONS, INC., Sunnyvale, CA (US)

(72) Inventor: Anthony Michael Jarc, Duluth, GA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/547,869

(22) Filed: Aug. 22, 2019

(65) Prior Publication Data
US 2020/0045301 A1 Feb. 6, 2020

Related U.S. Application Data

(62) Division of application No. 15/126,151, filed as application No. PCT/US2015/021315 on Mar. 18, 2015, now Pat. No. 10,432,922.
(Continued)

(51) Int. Cl.
*H04N 13/383* (2018.01)
*A61B 34/30* (2016.01)
(Continued)

(52) U.S. Cl.
CPC ......... *H04N 13/383* (2018.05); *A61B 3/0041* (2013.01); *A61B 3/113* (2013.01);
(Continued)

(58) Field of Classification Search
CPC ........ A61B 2034/742; A61B 2034/744; A61B 34/30; A61B 34/74; A61B 3/0041;
(Continued)

(56) References Cited

U.S. PATENT DOCUMENTS 5,204,942 A 4/1993 Otera et al.
5,553,609 A 9/1996 Chen et al.
(Continued)

FOREIGN PATENT DOCUMENTS

CN 102958464 A 3/2013
JP S61172552 A 8/1986
(Continued)

OTHER PUBLICATIONS

Chen J et al., et al., "A Robust 3D Eye Gaze Tracking System Using Noise Reduction," Eye Tracking Research & Applications: Proceedings ; ETRA 2008 ; [Eye Tracking Research and Applications Symposium]; Savanna, Georgia, USA, Mar. 26-28, 2008, ACM, New York, NY, Mar. 26, 2008 (Mar. 26, 2008), pp. 189-196, XP058345555, DOI: 10.1145/1 344471. 1, 1344518, ISBN: 978-1-59593-982-1.

(Continued)

*Primary Examiner* — Christopher S Kelley
*Assistant Examiner* — Kathleen M Walsh
(74) *Attorney, Agent, or Firm* — Haynes and Boone, LLP

(57) ABSTRACT

A teleoperational medical system comprises an eye tracking system, which includes: an image display comprising a first coordinate frame configured to display an image of a surgical field comprising a second coordinate frame to a user in a third coordinate frame; at least one right eye tracker configured to measure data about a first gaze point of a right eye of the user; at least one left eye tracker configured to measure data about a second gaze point of a left eye of the user; and at least one processor configured to process the data about the first and second gaze points to determine a viewing location in the displayed image at which the first and second gaze points are directed. The medical system further comprises a control unit configured to control at least (Continued)

one function of the medical system based upon the determined viewing location.

17 Claims, 11 Drawing Sheets

Related U.S. Application Data

(60) Provisional application No. 61/955,334, filed on Mar. 19, 2014.

(51) Int. Cl.

| | | |
|---|---|---|
| *A61B 3/113* | (2006.01) | |
| *G02B 27/00* | (2006.01) | |
| *A61B 34/00* | (2016.01) | |
| *H04N 13/239* | (2018.01) | |
| *G02B 21/00* | (2006.01) | |
| *G02B 27/01* | (2006.01) | |
| *G02B 30/35* | (2020.01) | |
| *H04N 13/243* | (2018.01) | |
| *A61B 3/00* | (2006.01) | |
| *A61B 5/00* | (2006.01) | |
| *G02B 21/22* | (2006.01) | |
| *G02B 30/34* | (2020.01) | |

(52) U.S. Cl.
CPC .............. *A61B 34/30* (2016.02); *A61B 34/74* (2016.02); *G02B 21/0012* (2013.01); *G02B 27/0093* (2013.01); *G02B 27/017* (2013.01); *G02B 30/35* (2020.01); *H04N 13/239* (2018.05); *H04N 13/243* (2018.05); *A61B 5/7445* (2013.01); *A61B 2034/742* (2016.02); *A61B 2034/744* (2016.02); *G02B 21/22* (2013.01); *G02B 30/34* (2020.01); *G02B 2027/0134* (2013.01); *G02B 2027/0138* (2013.01); *G02B 2027/0187* (2013.01)

(58) Field of Classification Search
CPC ....... A61B 3/113; A61B 5/7445; A61B 90/37; G02B 27/0093; G02B 27/2235; G02B 2027/0134; G02B 2020/0138; G02B 2027/0187; G02B 21/0012; G02B 21/22; G02B 27/017; G02B 27/2228; H04N 13/0239; H04N 13/0484; H04N 13/239; H04N 13/383
USPC .......................................................... 348/47
See application file for complete search history.

(56) References Cited

U.S. PATENT DOCUMENTS

| | | | |
|---|---|---|---|
| 5,704,791 A | 1/1998 | Gillio | |
| 5,855,553 A | 1/1999 | Tajima et al. | |
| 5,867,308 A | 2/1999 | Pensel et al. | |
| 5,876,325 A | 3/1999 | Mizuno et al. | |
| 5,931,832 A | 8/1999 | Jensen | |
| 6,090,051 A | 7/2000 | Marshall | |
| 6,459,926 B1 | 10/2002 | Nowlin et al. | |
| 6,578,962 B1 | 6/2003 | Amir et al. | |
| 6,659,939 B2 | 12/2003 | Moll et al. | |
| 6,799,065 B1 | 9/2004 | Niemeyer | |
| 6,852,107 B2 | 2/2005 | Wang et al. | |
| 6,892,112 B2 | 5/2005 | Wang et al. | |
| 6,951,535 B2 | 10/2005 | Ghodoussi et al. | |
| 7,245,202 B2 | 7/2007 | Levin | |
| 7,259,652 B2 | 8/2007 | Wang et al. | |
| 7,865,266 B2 | 1/2011 | Moll et al. | |
| 7,914,521 B2 | 3/2011 | Wang et al. | |
| 8,527,094 B2 | 9/2013 | Kumar et al. | |
| 8,831,782 B2 | 9/2014 | Itkowitz | |
| 8,914,150 B2 | 12/2014 | Moll et al. | |
| 9,039,681 B2 | 5/2015 | Wang et al. | |
| 9,107,633 B2 | 8/2015 | Mueller et al. | |
| 9,119,654 B2 | 9/2015 | Ramans et al. | |
| 9,307,894 B2 | 4/2016 | Von et al. | |
| 9,360,934 B2 * | 6/2016 | Ruiz Morales | A61B 34/30 |
| 1,027,878 A1 | 5/2019 | Jarc et al. | |
| 1,043,292 A1 | 10/2019 | Jarc | |
| 10,432,922 B2 * | 10/2019 | Jarc | A61B 3/0041 |
| 2002/0029095 A1 | 3/2002 | Kosaka et al. | |
| 2002/0105482 A1 | 8/2002 | Lemelson et al. | |
| 2003/0020755 A1 | 1/2003 | Lemelson et al. | |
| 2003/0050733 A1 | 3/2003 | Wang et al. | |
| 2003/0169213 A1 | 9/2003 | Spero | |
| 2005/0206583 A1 | 9/2005 | Lemelson et al. | |
| 2005/0228256 A1 | 10/2005 | Labadie et al. | |
| 2006/0082542 A1 | 4/2006 | Morita et al. | |
| 2006/0100642 A1 * | 5/2006 | Yang | A61B 34/70 |
| | | | 606/130 |
| 2006/0109237 A1 | 5/2006 | Morita et al. | |
| 2006/0166681 A1 | 7/2006 | Lohbihler | |
| 2006/0258938 A1 | 11/2006 | Hoffman | |
| 2008/0253519 A1 | 10/2008 | Bonfiglio et al. | |
| 2009/0036902 A1 | 2/2009 | DiMaio et al. | |
| 2009/0248036 A1 * | 10/2009 | Hoffman | A61B 1/00149 |
| | | | 606/130 |
| 2009/0268010 A1 | 10/2009 | Zhao et al. | |
| 2009/0270678 A1 * | 10/2009 | Scott | A61B 1/043 |
| | | | 600/109 |
| 2011/0020779 A1 | 1/2011 | Hannaford et al. | |
| 2011/0041160 A1 | 2/2011 | Choi et al. | |
| 2011/0118748 A1 | 5/2011 | Itkowitz et al. | |
| 2011/0228051 A1 | 9/2011 | Dedeoglu et al. | |
| 2011/0299034 A1 * | 12/2011 | Walsh | A61B 3/0091 |
| | | | 351/206 |
| 2012/0069166 A1 | 3/2012 | Kunz et al. | |
| 2012/0147328 A1 | 6/2012 | Yahav | |
| 2013/0023899 A1 | 1/2013 | Green | |
| 2013/0030571 A1 * | 1/2013 | Ruiz Morales | G06F 3/0482 |
| | | | 700/259 |
| 2013/0107207 A1 | 5/2013 | Zhao et al. | |
| 2013/0114850 A1 | 5/2013 | Publicover et al. | |
| 2013/0331859 A1 | 12/2013 | Kumar et al. | |
| 2014/0024889 A1 * | 1/2014 | Xiaoli | A61B 1/3132 |
| | | | 600/102 |
| 2014/0160004 A1 | 6/2014 | Katz et al. | |
| 2014/0160434 A1 | 6/2014 | Brown, Jr. et al. | |
| 2014/0163736 A1 | 6/2014 | Azizian et al. | |
| 2014/0275760 A1 | 9/2014 | Lee et al. | |
| 2014/0375789 A1 * | 12/2014 | Lou | G02B 27/017 |
| | | | 348/78 |
| 2015/0173846 A1 * | 6/2015 | Schneider | G02B 27/0101 |
| | | | 600/424 |
| 2016/0183930 A1 | 6/2016 | Herzlinger et al. | |
| 2017/0172675 A1 | 6/2017 | Jarc et al. | |
| 2019/0223968 A1 | 7/2019 | Jarc et al. | |

FOREIGN PATENT DOCUMENTS

| | | | |
|---|---|---|---|
| JP | 07328016 A * | 12/1995 | |
| JP | H07328016 A | 12/1995 | |
| WO | WO-2010051037 A1 | 5/2010 | |
| WO | WO-2011125007 A1 | 10/2011 | |
| WO | WO-2012160741 A1 | 11/2012 | |
| WO | WO-2013175465 A1 | 11/2013 | |
| WO | WO-2014037953 A2 * | 3/2014 | ............ A61B 5/748 |
| WO | WO-2015143067 A1 | 9/2015 | |
| WO | WO-2015143073 A1 | 9/2015 | |

OTHER PUBLICATIONS

English language translation of Office Action dated Jan. 8, 2019 for Japanese Application No. JP20160558123 filed Mar. 18, 2015, 9 pages.

(56) References Cited

OTHER PUBLICATIONS

Extended European Search Report for Application No. EP15765508.5, dated Mar. 6, 2018, 14 pages.
International Preliminary Report on Patentability for Application No. PCT/US15/21309, dated Sep. 29, 2016, 14 pages.
International Preliminary Report on Patentability for Application No. PCT/US15/21315, dated Sep. 29, 2016, 10 pages.
International Search Report and Written Opinion for Application No. PCT/US15/21309, dated Jun. 26, 2015, 17 pages.
International Search Report and Written Opinion for Application No. PCT/US15/21315, dated Aug. 25, 2015, 14 pages.
Kohlbecher S., et al., "Calibration-Free Eye Tracking by Reconstruction of the Pupil Ellipse in 3DSpace," Eye Tracking Research & Applications: Proceedings; ETRA 2008; [Eye Tracking Research and Applications Symposium]; Savanna, Georgia, USA, Mar. 26-28, 2008, ACM, New York, NY, Mar. 26, 2008 (Mar. 26, 2008), pp. 135-138, XP058345545,DOI: 10.1145/1344471.1344506, ISBN: 978-1-59593-982-1.
Ahmidi N., et al. "Surgical Task and Skill Classification from Eye Tracking and Tool Motion in Minimally Invasive Surgery," Medical Image Computing and Computer-Assisted Intervention—MICCAI, 2010, vol. 6363, pp. 295-302.
Partial Supplementary European Search Report for Application No. 15765508.5, dated Dec. 1, 2017, 17 pages.
Reiley C.E., et al., "Review of Methods for Objective Surgical Skill Evaluation," Surgical Endoscopy, Feb. 2011, vol. 25, pp. 356-366.
Extended European Search Report for Application No. EP15765996.2, dated Nov. 17, 2017, 9 pages.
Hansen D.W, et al., "In the Eye of the Beholder: A Survey of Models for Eyes and Gaze," IEEE Transactions on Pattern Analysis and Machine Intelligence. IEEE Computersociety, USA, vol. 32 (3), Mar. 1, 2010 (Mar. 1, 2010), pp. 478-500, XP011280658, ISSN: 0162-8828, DOI: 10.1109/TPAMI. 2009.30.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

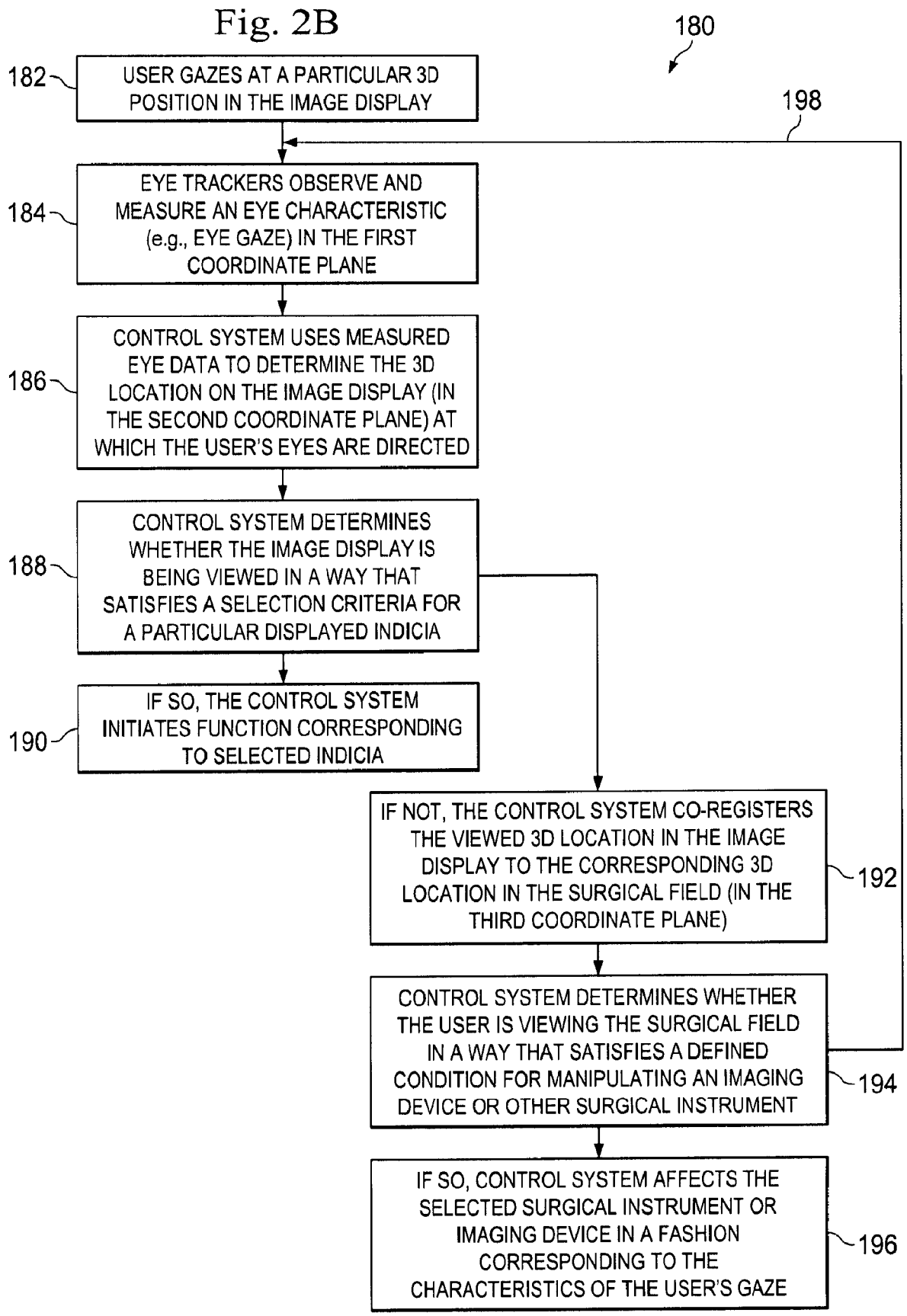

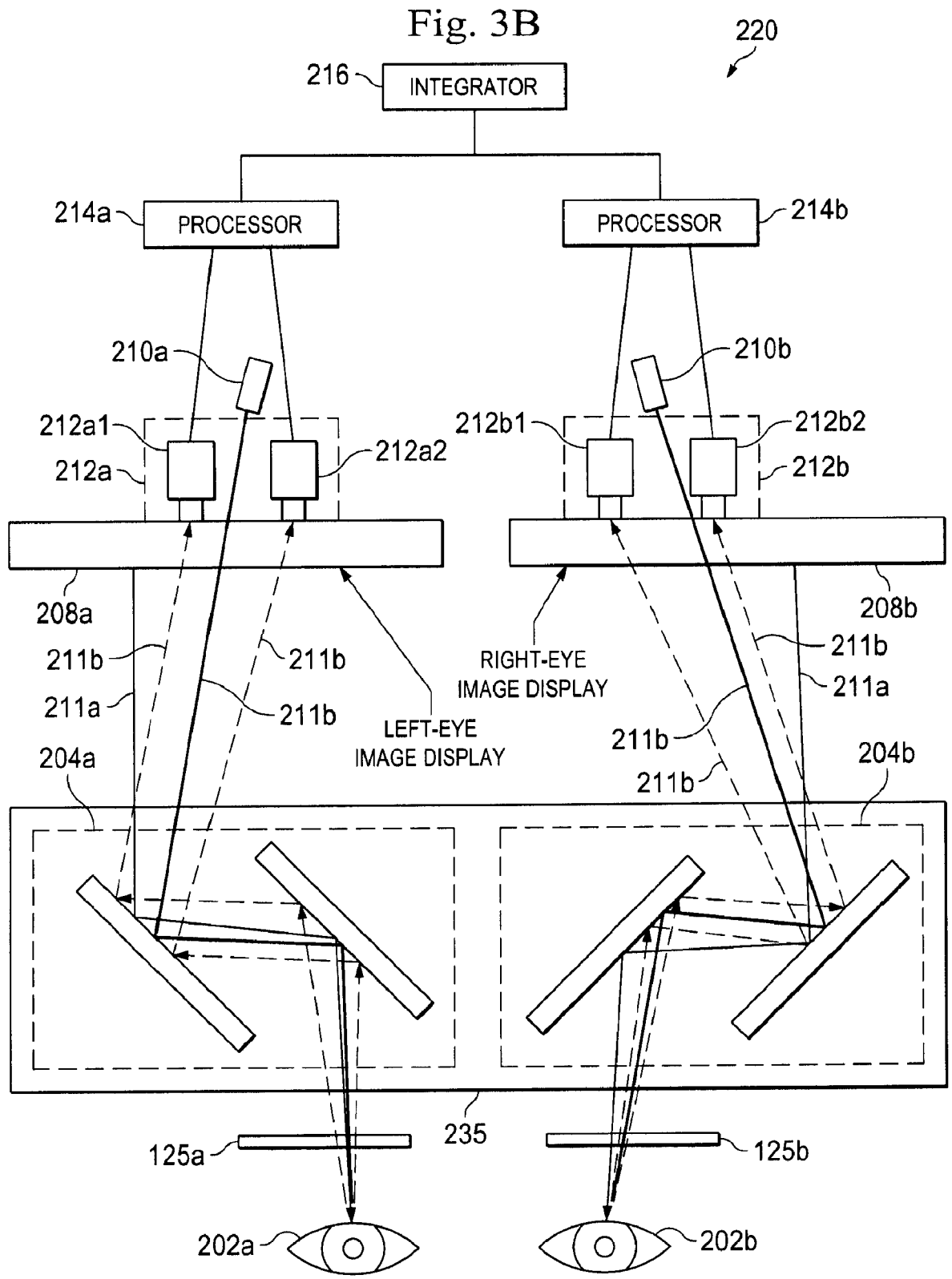

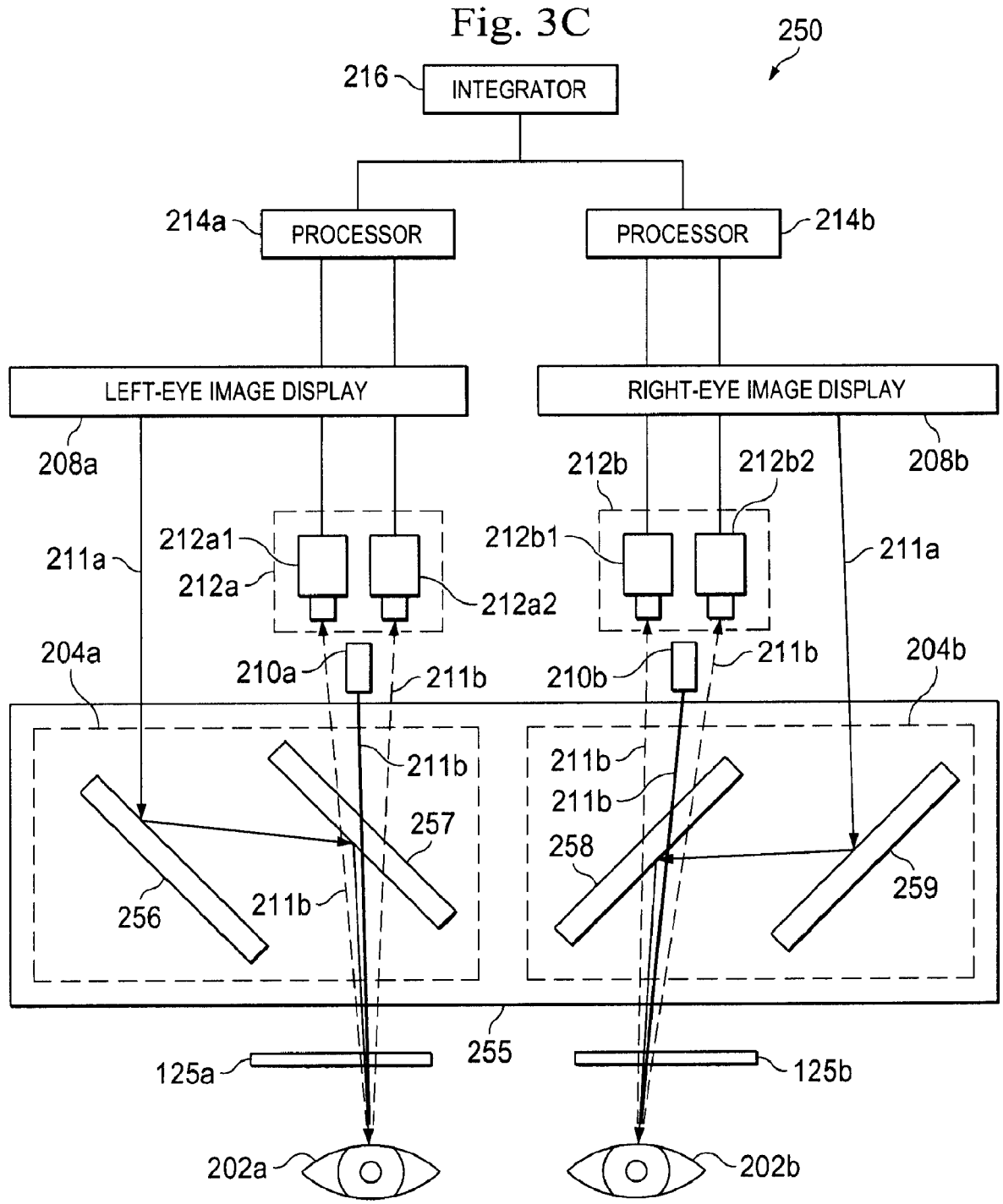

MEDICAL DEVICES, SYSTEMS, AND METHODS USING EYE GAZE TRACKING FOR STEREO VIEWER

RELATED APPLICATIONS

This application is a division of U.S. patent application Ser. No. 15/126,151 filed Sep. 14, 2016, which is the U.S. national phase of International Application No. PCT/US2015/021315, filed Mar. 18, 2015, which designated the U.S. and claims priority to U.S. Provisional Patent Application No. 61/955,334 entitled "Medical Devices, Systems, and Methods Integrating Eye Gaze Tracking for Stereo Viewer" filed Mar. 19, 2014, which are incorporated by reference herein, in their entirety.

BACKGROUND

Surgical procedures can be performed using a teleoperational medical system in a minimally invasive manner. The benefits of a minimally invasive surgery are well known and include less patient trauma, less blood loss, and faster recovery times when compared to traditional, open incision surgery. In addition, the use of a teleoperational medical system, such as the DA VINCI® Surgical System commercialized by Intuitive Surgical, Inc., Sunnyvale, Calif., is known. Such teleoperational medical systems may allow a surgeon to operate with intuitive control and increased precision when compared to manual minimally invasive surgeries.

A teleoperational medical system may include one or more instruments that are coupled to one or more robotic arms. If the system is used to perform minimally invasive surgery, the instruments may access the surgical area through one or more small openings in the patient, such as small incisions or natural orifices, such as, for example, the mouth, urethra, or anus. In some cases, rather than having the instrument(s) directly inserted through the opening(s), a cannula or other guide element can be inserted into each opening and the instrument can be inserted through the cannula to access the surgical area. An imaging tool such as an endoscope can be used to view the surgical area, and the image captured by the imaging tool can be displayed on an image display to be viewed by the surgeon during a surgery.

It is desirable to provide teleoperational medical systems that can effectively and accurately employ eye gaze tracking for various applications during minimally invasive medical procedures. The systems and methods disclosed herein overcome one or more of the deficiencies of the prior art.

SUMMARY

In one exemplary aspect, the present disclosure is directed to an eye tracking system comprising an image display configured to display an image of a surgical field to a user. The image display is configured to emit a light in first wavelength range. The system further comprises a right eye tracker configured to emit light in a second wavelength range and to measure data about a first gaze point of a right eye of the user. The system further comprises a left eye tracker configured to emit light in the second wavelength range and to measure data about a second gaze point of a left eye of the user. The system further comprises an optical assembly disposed between the image display and the right and left eyes of user. The optical assembly is configured to direct the light of the first and second wavelength ranges such that the first and second wavelengths share at least a portion of a left optical path between left eye and the image display and share at least a portion of a right optical path between the right eye and the image display, without the right and left eye trackers being visible to the user. The system further comprises at least one processor configured to process the data about the first gaze point and the second gaze point to determine a viewing location in the displayed image at which the gaze point of the user is directed.

In another exemplary aspect, the present disclosure is directed to an eye tracking system comprising an image display configured to display a stereo image of a surgical field to a user. The system also comprises at least one right eye tracker configured to measure data about a first gaze point of a right eye of the user and at least one left eye tracker configured to measure data about a second gaze point of a left eye of the user. The system also comprises a right eye light emitter and a left eye light emitter. The right eye light emitter configured to emit light of a first wavelength range to the right eye of the user, and the left eye light emitter configured to emit light of a first wavelength range to the left eye of the user. The system also comprises an optical assembly positioned between the image display and the eyes of the user. The optical assembly comprising a right eye mirror set and a left eye mirror set arranged to provide optical communication between the eyes of the user, the eye trackers, and the light emitters. The system also comprises at least one processor configured to process the data about the first gaze point and the second gaze point to determine a viewing location in the displayed stereo image at which the gaze point of the user is directed.

These and other embodiments are further discussed below with respect to the following figures.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the 5 dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 1B illustrates a front elevation view of an exemplary teleoperational assembly according to one embodiment of the present disclosure. FIG. 1C illustrates a front elevation view of an exemplary operator input system according to one embodiment of the present disclosure. FIG. 1D illustrates a front view of an exemplary vision cart component according to one embodiment of the present disclosure.

FIG. 2B is a flowchart illustrating an exemplary method of using the eye tracking units to affect the teleoperational system and/or a surgical instrument according to one embodiment of the present disclosure.

FIGS. 3A-3D schematically illustrate various embodiments of an eye tracking system of the stereo viewer used by the teleoperational medical system of FIGS. 1A, 1B, and 1C according to the present disclosure.

DETAILED DESCRIPTION

Figure 1A:
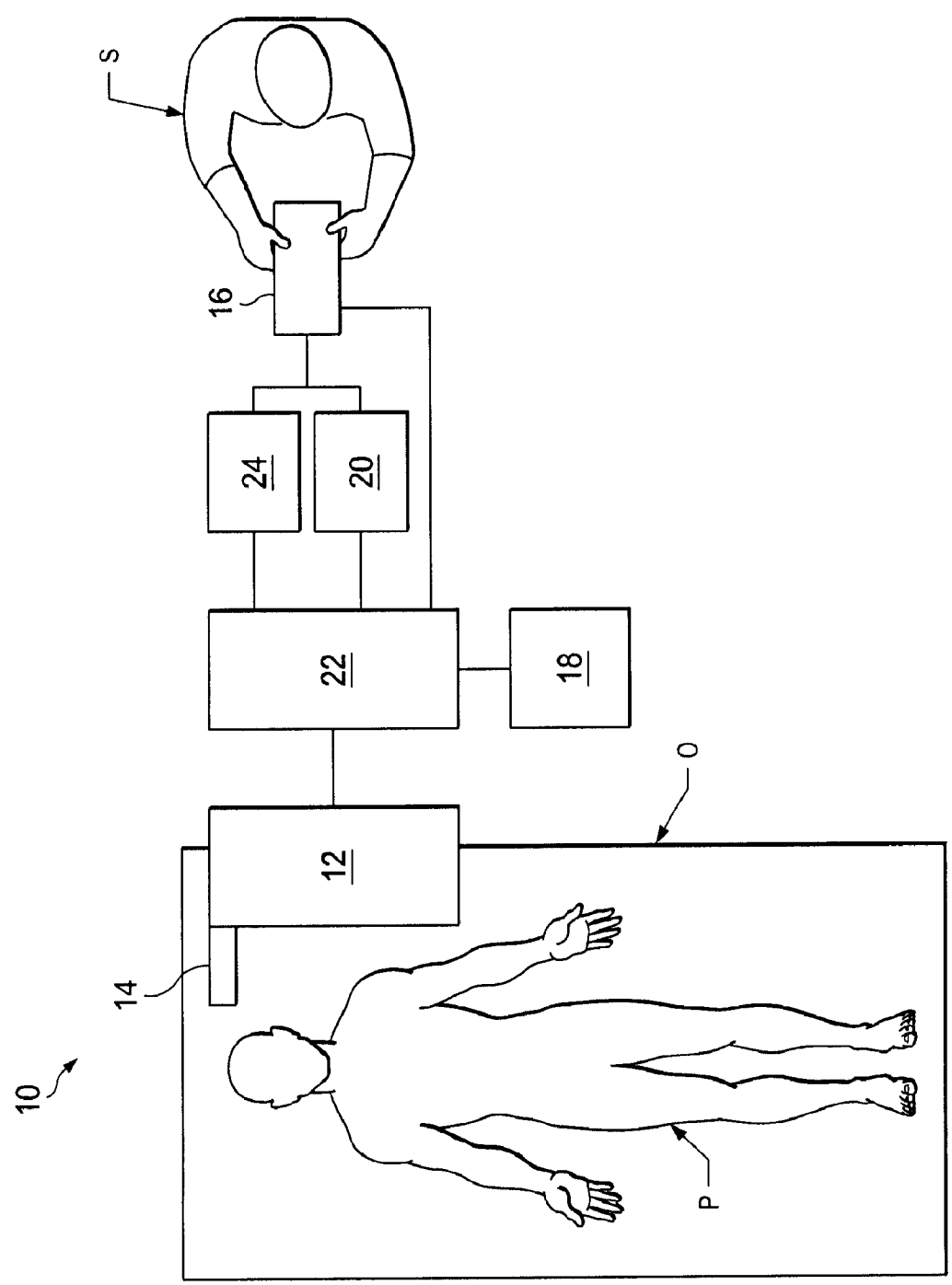
FIG. 1A illustrates an exemplary teleoperational medical system according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the disclosure.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers 30 to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

It will be appreciated that the terms "proximal" and "distal" are used herein with reference to a clinician manipulating an end of an instrument extending from the clinician to a surgical site. The term "proximal" refers to the portion of the instrument closer to the clinician, and the term "distal" refers to the portion of the instrument further away from the clinician and closer to the surgical site. For conciseness and clarity, spatial terms such as "horizontal," "vertical," "above," and "below" may be used herein with respect to the drawings. However, surgical instruments are used in many orientations and positions, and these terms are not intended to be limiting and absolute.

The present disclosure relates generally to using eye tracking systems to observe and measure characteristics of a user's eyes (e.g., eye gaze tracking) during the use of teleoperational medical systems and/or instruments used in a variety of medical procedures, including without limitation diagnostic, surgical, and/or therapeutic procedures. In particular, in some embodiments, the eye tracking systems disclosed herein rely on the ability to track the accurate location (e.g., 2D or 3D location) of the user's eye gaze on a surgical console. In some embodiments, the eye tracking systems may be used to control the teleoperational system by directly operating the system instruments and/or by influencing system characteristics to effect system-wide changes. In particular, some embodiments of the present disclosure are related to system and instrument control by accurately tracking the operator's eye gaze on a surgical console while the operator uses a teleoperational medical system during a minimally invasive procedure.

In a teleoperated surgical system, the eye gaze points of the surgeon may be tracked during a surgery by one or more eye trackers, such as stereo cameras. However, eye gaze tracking may be inaccurate due to various factors, including, by way of non-limiting example, changes in the head position of the user and the separate image displays for each eye (e.g., creating a stereo view). For example, the pupil's position and corneal reflection of a surgeon's eye can be determined by a combination of the surgeon's head and eye orientation. In many cases, the head motions of the surgeon, the head pressure of the surgeon upon the console, and/or image occlusion by the eye trackers during a surgery may compromise accurate and effective eye gaze tracking using conventional techniques. Conventionally, eye gaze tracking techniques require an external device disposed out of the teleoperated surgical system to be used during an eye tracking process. For example, the external device may be mounted on a pair of glasses that are worn by the surgeon during a surgery. There is usually a distance and a relative motion between the external eye tracking device and the surgeon's eyes. Therefore, this kind of external eye tracking device may not only create inconvenience and an uncomfortable feeling to the surgeon, and may also affect the accuracy of the surgeon's operation. Alternatively, the conventional eye gaze tracking device may be located near the eyepieces. This configuration may create interference to the surgeon's vision when the surgeon is looking into the eyepieces. For example, the edges of the eye gaze tracking device may appear in the surgeon's vision, which could distract the surgeon or compromise his or her view of the surgical field. In some embodiments, the eye gaze tracking devices described herein are configured to enable the eye trackers to share at least part of the same optical path as the displayed image while remaining invisible to the surgeon.

The embodiments disclosed herein improve the accuracy of eye tracking devices by compensating for common error-inducing factors such as, by way of non-limiting example, user head movements, head pressure, image occlusion by cameras or trackers, and/or the independent image displays to each eye. The embodiments described herein account for these error-inducing factors by using a model to more accurately predict the 3D eye gaze location based on positional data obtained from one or more eye trackers for each eye and the assumption of constant interpupillary distance (and/or other eye tracking characteristics). In particular, each eye of the user is measured by its own, independent eye tracker. Those of skill in the art will realize that the eye tracking systems disclosed herein may be utilized in similar (e.g., non-teleoperational) applications benefiting from more accurate gaze-assisted system and/or instrument control. By utilizing the eye tracking systems and methods disclosed herein, a user may experience more intuitive and more efficient interaction with a teleoperational medical system.

According to various embodiments, minimally invasive medical procedures may be performed using a teleoperational system to guide instrument delivery and operation. Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1, the teleoperational medical system 10 generally includes a teleoperational assembly 12 near or mounted to an operating table O on which a patient P is positioned. The teleoperational assembly 12 may be referred to as a patient-side manipulator (PSM). A medical instrument system 14 is operably coupled to the teleoperational assembly 12. An operator input system 16 allows a surgeon or other type of clinician S to view images of or representing the surgical site and to control the operation of the medical instrument system 14. The operator input system 16 may be referred to as a master or surgeon's console. One example of a teleoperational surgical system that can be used to implement the systems and techniques described in this disclosure is a da Vinci® Surgical System manufactured by Intuitive Surgical, Inc. of Sunnyvale, Calif.

The teleoperational assembly 12 supports the medical instrument system 14 and may include a kinematic structure of one or more non-servo controlled links (e.g., one or more links that may be manually positioned and locked in place, generally referred to as a set-up structure) and a teleoperational manipulator. (See, e.g., FIG. 2) The teleoperational assembly 12 includes plurality of motors that drive inputs on the medical instrument system 14. These motors move in response to commands from a control system 22. The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument.

The teleoperational medical system 10 also includes an image capture system 18 which includes an image capture device, such as an endoscope, and related image processing hardware and software. The teleoperational medical system 10 also includes a control system 22 that is operatively linked to sensors, motors, actuators, and other components of the teleoperational assembly 12, the operator input system 16 and to the image capture system 18.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. More specifically, in response to the surgeon's input commands, the control system 22 effects servomechanical movement medical instrument system 14. The control device(s) may include one or more of any number of a variety of input devices, such as hand grips, joysticks, trackballs, data gloves, trigger-guns, hand-operated controllers, foot-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The system operator sees images, captured by the image capture system 18, presented for viewing on a display system 20 operatively coupled to or incorporated into the operator input system 16. The display system 20 displays an image or representation of the surgical site and medical instrument system(s) 14 generated by sub-systems of the image capture system 18. The display system 20 and the operator input system 16 may be oriented so the operator can control the medical instrument system 14 and the operator input system 16 with the perception of telepresence. The display system 20 may include multiple displays such as separate right and left displays for presenting separate images to each eye of the operator, thus allowing the operator to view stereo images.

Alternatively or additionally, display system 20 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented preoperative or intra-operative images may include two-dimensional, three-dimensional, or four-dimensional (including e.g., time based or velocity based information) images and associated image data sets for reproducing the images.

The control system 22 includes at least one memory and at least one processor (not shown), and typically a plurality of processors, for effecting control between the teleoperational system 12, medical instrument system 14, the operator input system 16, the image capture system 18, and the display system 20. The control system 22 also includes programmed instructions (e.g., a computer-readable medium storing the instructions) to implement some or all of the methods described in accordance with aspects disclosed herein. While control system 22 is shown as a single block in the simplified schematic of FIG. 1, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 22 supports wireless communication protocols such as Bluetooth, IrDA, HomeRF, IEEE 802.11, DECT, and Wireless Telemetry.

In some embodiments, control system 22 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

In this embodiment, the teleoperational medical system 10 also includes an eye tracking unit 24 which may be operatively coupled to or incorporated into the operator input system 16. The eye tracking unit 24 is operatively coupled to the control system 22 for sensing, measuring, recording, and conveying information related to the operator's eyes while the operator is viewing the display 20 and/or operating the operator controls at the operator input system 16.

The teleoperational medical system 10 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be co-located or they may be positioned in separate locations. Multiple operator input systems allow more than one operator to control one or more manipulator assemblies in various combinations.

Figure 1B:
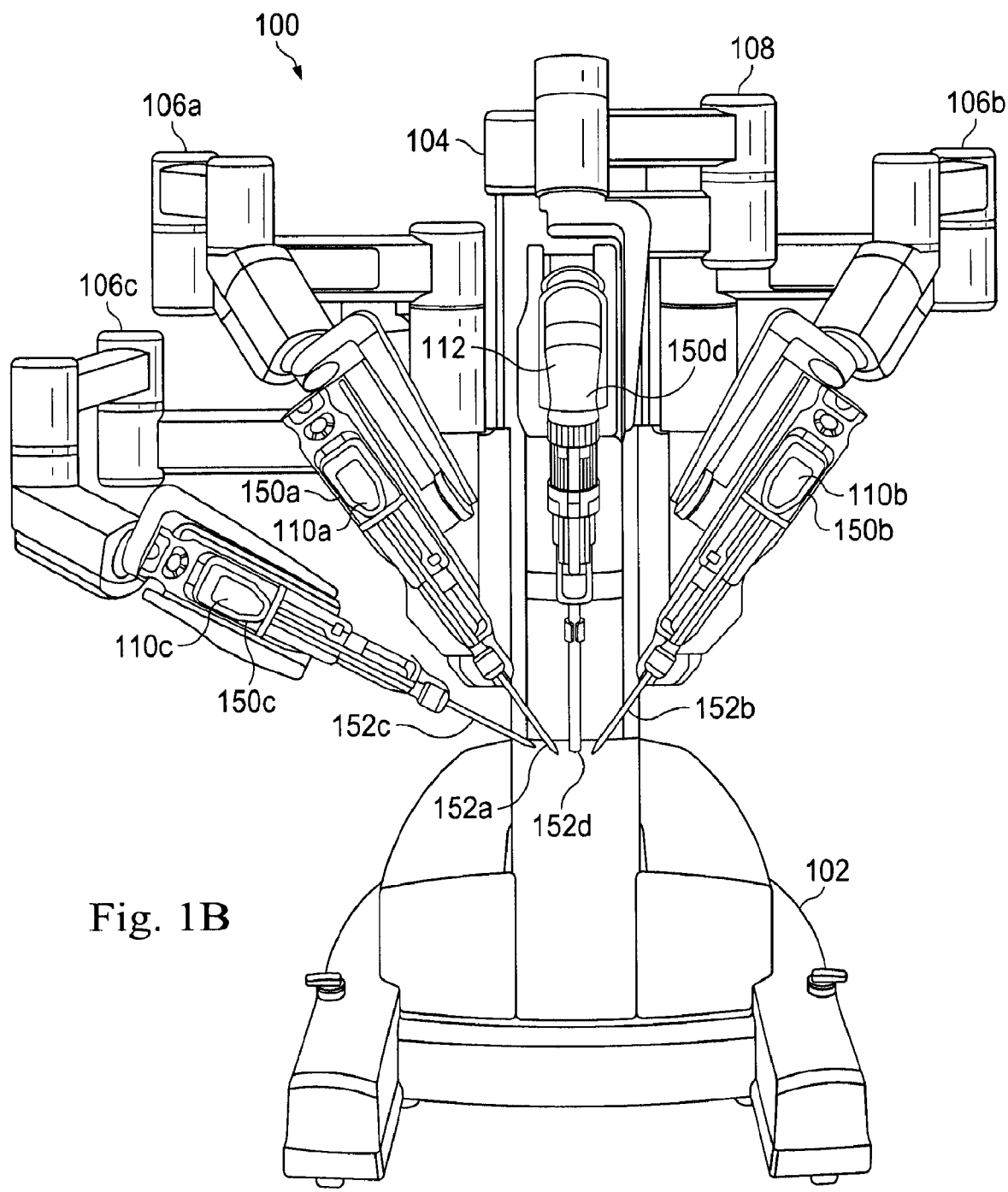
FIGS. 1B, 1C, and 1D illustrate exemplary components of a teleoperational medical system according to various embodiments of the present disclosure. In particular.

FIG. 1B is a front elevation view of a teleoperational assembly 100 (e.g., the teleoperational assembly 12 shown in FIG. 1A) according to one embodiment. The assembly 100 includes a base 102 that rests on the floor, a support tower 104 that is mounted on the base 102, and several arms that support surgical tools (including portions of the image capture system 18). As shown in FIG. 1B, arms 106a, 106b, 106c are instrument arms that support and move the surgical instruments used to manipulate tissue, and arm 108 is a camera arm that supports and moves the endoscope. FIG. 1B further shows interchangeable surgical instruments 110a, 110b, 110c mounted on the instrument arms 106a, 106b, 106c, respectively, and it shows an endoscope 112 mounted on the camera arm 108. The endoscope 112 may be a stereo endoscope for capturing stereo images of the surgical site and providing the separate stereo images to the display system 20. Knowledgeable persons will appreciate that the arms that support the instruments and the camera may also be supported by a base platform (fixed or moveable) mounted to a ceiling or wall, or in some instances to another piece of equipment in the operating room (e.g., the operating table). Likewise, they will appreciate that two or more separate bases may be used (e.g., one base supporting each arm).

Figure 1C:
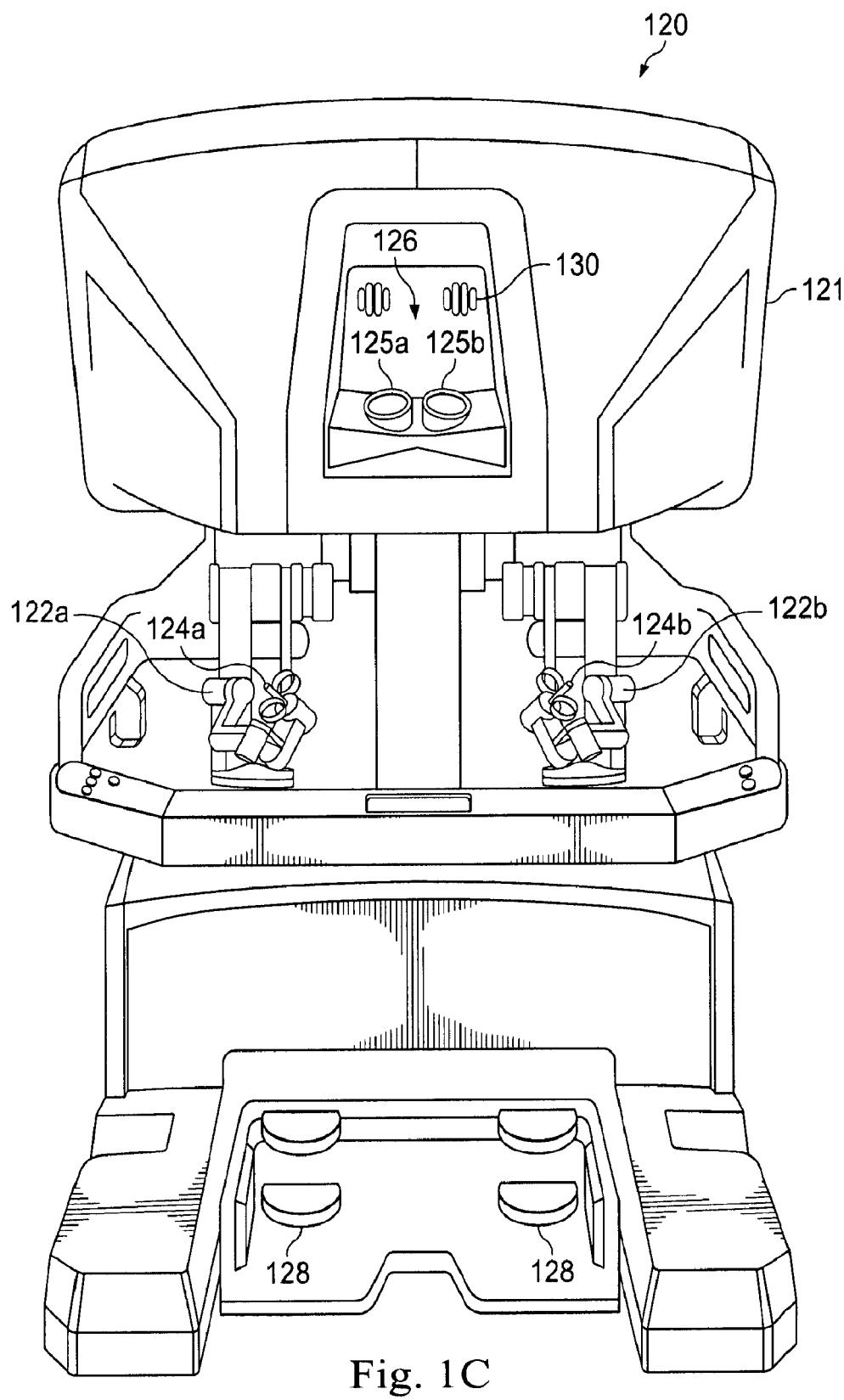

As is further illustrated in FIG. 1B, the instruments 110a, 110b, 110c, and the endoscope 112 include instrument interfaces 150a, 150b, 150c, and 150d, respectively, and instrument shafts 152a, 152b, 152c, and 152d, respectively. In some embodiments, the teleoperational assembly 100 may include supports for cannulas that fix the instruments 110a, 110b, 110c, and the endoscope 112 with respect to the cannulas. In some embodiments, portions of each of the instrument arms 106a, 106b, 106c, and 108 may be adjustable by personnel in the operating room in order to position the instruments 110a, 110b, 110c, and the endoscope 112 with respect to a patient. Other portions of the arms 106a, 106b, 106c, and 108 may be actuated and controlled by the operator at an operator input system 120 (as shown in FIG. 1C). The surgical instruments 110a, 110b, 110c, and endoscope 112, may also be controlled by the operator at the operator input system 120.

FIG. 1C is a front elevation view of an operator input system 120 (e.g., the operator input system 16 shown in FIG. 1A). The operator input system 120 includes a console 121 equipped with left and right multiple degree-of-freedom (DOF) control interfaces 122a and 122b, which are kinematic chains that are used to control the surgical instruments 110a, 110b, 110c, and the endoscope 112. The surgeon grasps a pincher assembly 124a, 124b on each of control interfaces 122, typically with the thumb and forefinger, and can move the pincher assembly to various positions and orientations. When a tool control mode is selected, each of control interfaces 122 is configured to control a corresponding surgical instrument and instrument arm 106. For example, a left control interface 122a may be coupled to control the instrument arm 106a and the surgical instrument 110a, and a right control interface 122b may be coupled to the control instrument arm 106b and the surgical instrument 110b. If the third instrument arm 106c is used during a surgical procedure and is positioned on the left side, then left control interface 122a can be switched from controlling the arm 106a and the surgical instrument 110a to controlling the arm 106c and the surgical instrument 110c. Likewise, if the third instrument arm 106c is used during a surgical procedure and is positioned on the right side, then the right control interface 122a can be switched from controlling the arm 106b and surgical instrument 110b to controlling the arm 106c and the surgical instrument 110c. In some instances, control assignments between the control interfaces 122a, 122b and combination of arm 106a/surgical instrument 110a and combination of arm 106b/surgical instrument 110b may also be exchanged. This may be done, for example, if the endoscope is rolled 180 degrees, so that the instrument moving in the endoscope's field of view appears to be on the same side as the control interface the surgeon is moving. The pincher assembly is typically used to operate a jawed surgical end effector (e.g., scissors, grasping retractor, and the like) at the distal end of a surgical instrument 110.

Additional controls are provided with foot pedals 128. Each of foot pedals 128 can activate certain functionality on the selected one of instruments 110. For example, foot pedals 128 can activate a drill or a cautery tool or may operate irrigation, suction, or other functions. Multiple instruments can be activated by depressing multiple ones of pedals 128. Certain functionality of instruments 110 may be activated by other controls.

The surgeon's console 120 also includes a stereo image viewer system 126 (e.g., the display system 20 shown in FIG. 1A). Stereo image viewer system 126 includes a left eyepiece 125a and a right eyepiece 125b, so that the surgeon may view left and right stereo images using the surgeon's left and right eyes respectively inside the stereo image viewer system 126. Left side and right side images captured by endoscope 112 are outputted on corresponding left and right image displays, which the surgeon perceives as a three-dimensional image on a display system (e.g., the display system 20 shown in FIG. 1A In an advantageous configuration, the control interfaces 122 are positioned below stereo image viewer system 126 so that the images of the surgical tools shown in the display appear to be located near the surgeon's hands below the display. This feature allows the surgeon to intuitively control the various surgical instruments in the three-dimensional display as if watching the hands directly. Accordingly, the servo control of the associated instrument arm and instrument is based on the endoscopic image reference frame.

The endoscopic image reference frame is also used if the control interfaces 122 are switched to a camera control mode. In some cases, if the camera control mode is selected, the surgeon may move the distal end of endoscope 112 by moving one or both of the control interfaces 122 together. The surgeon may then intuitively move (e.g., pan, tilt, zoom) the displayed stereoscopic image by moving the control interfaces 122 as if holding the image in his or her hands.

As is further shown in FIG. 1C, a headrest 130 is positioned above stereo image viewer system 126. As the surgeon is looking through stereo image viewer system 126, the surgeon's forehead is positioned against headrest 130. In some embodiments of the present disclosure, manipulation of endoscope 112 or other surgical instruments can be achieved through manipulation of headrest 130 instead of utilization of the control interfaces 122. In some embodiments, the headrest 130 can, for example, include pressure sensors, a rocker plate, optically monitored slip plate, or other sensors that can detect movement of the surgeon's head. Additional details on using a sensing method to manipulate the headrest in order to control the endoscope camera may be found, for example, in U.S. Application No. 61/865,996, entitled "ENDOSCOPE CONTROL SYSTEM," which is incorporated herein by reference.

Figure 1D:
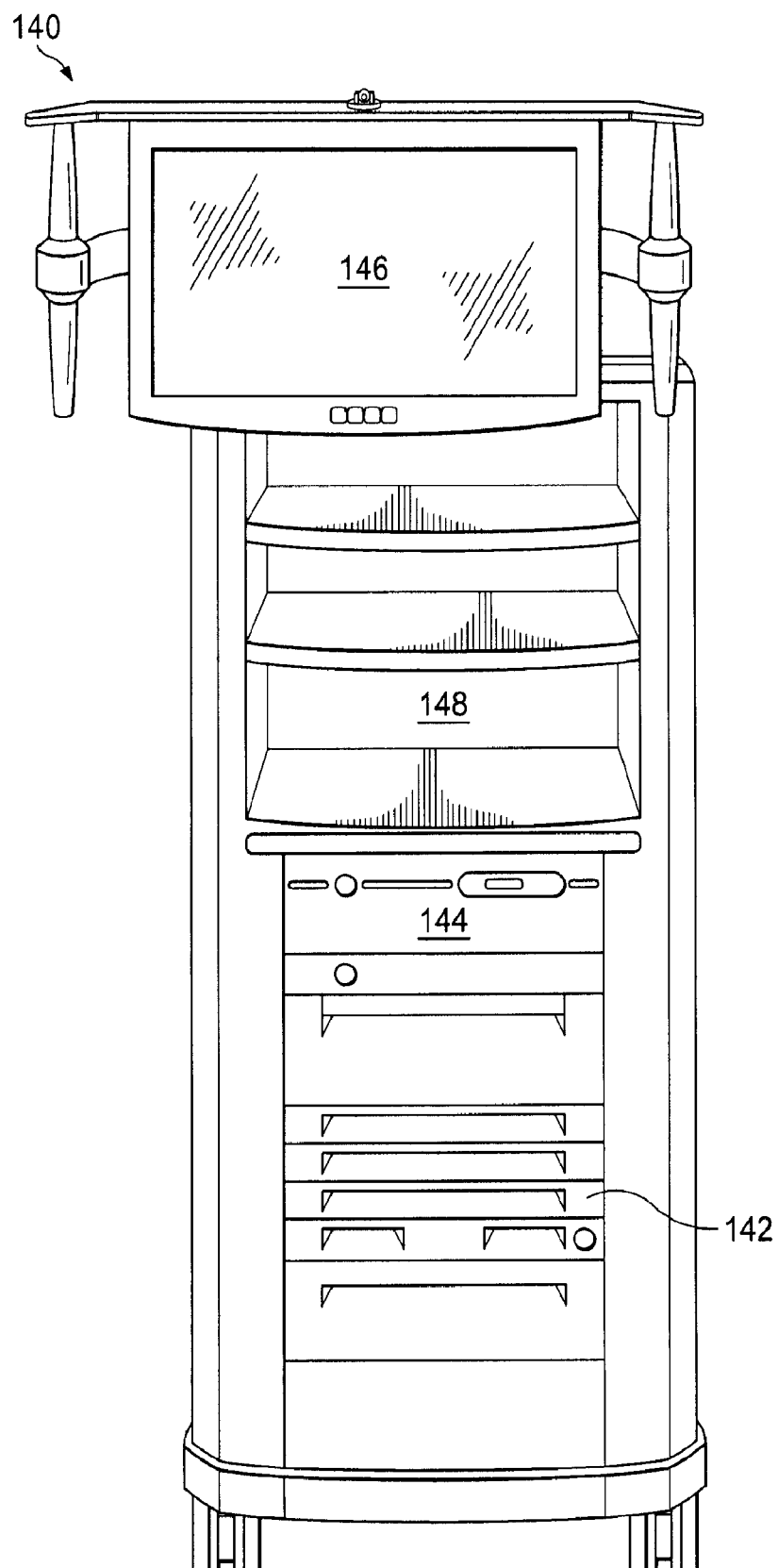

FIG. 1D is a front view of a vision cart component 140 of a surgical system. For example, in one embodiment, the vision cart component 140 is part of the medical system 10 shown in FIG. 1A. The vision cart 140 can house the surgical system's central electronic data processing unit 142 (e.g., all or portions of control system 22 shown in FIG. 1A) and vision equipment 144 (e.g., portions of the image capture system 18 shown in FIG. 1A). The central electronic data processing unit 142 includes much of the data processing used to operate the surgical system. In various implementations, however, the electronic data processing may be distributed in the surgeon console 120 and teleoperational assembly 100. The vision equipment 144 may include camera control units for the left and right image capture functions of the endoscope 112. The vision equipment 144 may also include illumination equipment (e.g., a Xenon lamp) that provides illumination for imaging the surgical site. As shown in FIG. 1D, the vision cart 140 includes an optional touch screen monitor 146 (for example a 24-inch monitor), which may be mounted elsewhere, such as on the assembly 100 or on a patient side cart. The vision cart 140 further includes space 148 for optional auxiliary surgical equipment, such as electrosurgical units, insufflators, suction irrigation instruments, or third-party cautery equipment. The teleoperational assembly 100 and the surgeon's console 120 are coupled, for example via optical fiber communications links, to the vision cart 140 so that the three components together act as a single teleoperated minimally invasive surgical system that provides an intuitive telepresence for the surgeon.

Note that in some embodiments, some or all of the assembly 100 of the teleoperated surgical system can be implemented in a virtual (simulated) environment, wherein some or all of the image seen by the surgeon at the surgeon's console 120 can be synthetic images of instruments and/or anatomy. In some embodiments, such synthetic imagery can be provided by the vision cart component 140 and/or directly generated at the surgeon's console 120 (e.g., via a simulation module).

During a typical minimally invasive surgical procedure with the teleoperated surgical system described with reference to FIGS. 1A-1D, at least two incisions are made into the patient's body (usually with the use of a trocar to place the associated cannula). One incision is for the endoscope camera instrument, and the other incisions are for the surgical instruments. In some surgical procedures, several instrument and/or camera ports are used to provide access and imaging for a surgical site. Although the incisions are relatively small in comparison to larger incisions used for traditional open surgery, a minimum number of incisions is desired to further reduce patient trauma and for improved cosmesis. In other embodiments, the teleoperational medical system 10 may be used with single incision access to the patient anatomy or with access through natural orifices such as the nose, mouth, anus, vagina, etc.

During a typical teleoperated surgery, it is often necessary for a surgeon to physically manipulate various controls to control the surgical system, the imaging devices, and/or the other surgical instruments associated with the system. For example, a surgeon may need to adjust the field of view of the imaging device by physically manipulating controls to guide and influence the device. The surgeon may use his or her hand to manually control a joystick or mouse, or his or her foot to tap a foot pedal at the surgeon's console to log-in to the surgical system, to search for a target surgical site within the view of the endoscope, to operate the movement of a surgical instrument such as a clamp, and/or to adjust the system settings or display settings. The conventional methods require the surgeon to free one hand from surgical operation, or to use one foot to tap the foot pedal, both of which may unnecessarily delay or disrupt the surgical operation. For example, the hand or foot action may redirect the surgeon's gaze and attention from the target surgical site to the surgeon's console, which could delay or disrupt the operation. After performing the required manual adjustment, the surgeon may need to spend additional time refocusing his or her attention and gaze point on the target surgical site.

Embodiments disclosed herein utilize gaze detection to enhance the way one or more users (e.g., surgeons and/or trainers) interface with the surgical system By translating the user's eye gaze (e.g., the location of a user's eye gaze relative to a display system or other surgical system component) into commands directed to the surgical system, embodiments disclosed herein may enable faster and more efficient control over the teleoperational medical system 10 than provided by conventional control methods. Eye tracking, or eye-gaze tracking, is the process of measuring either point-of-gaze (POG) (i.e., where the user is looking, typically in 3D space), or the motion of an eye relative to a head. In other words, POG is the point in space where a person's gaze is directed to, and has also been defined as the point in space that is imaged on the center of the highest acuity region of the retina (i.e., the fovea) of each eye.

Figure 2A:
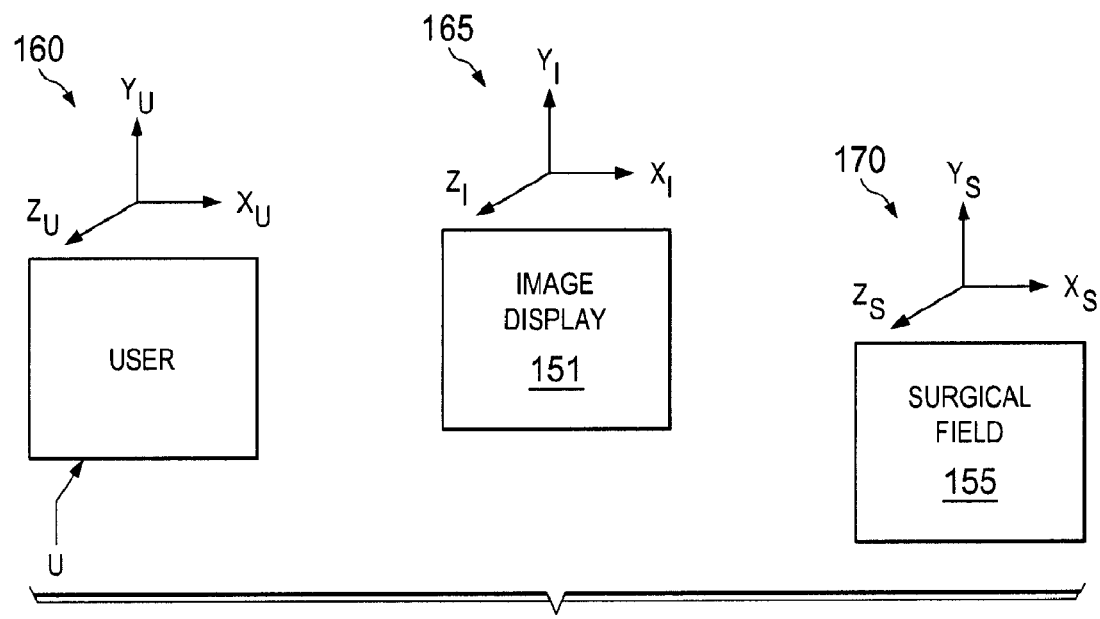
FIG. 2A illustrates a block diagram of the 3D coordinate frames of a user relative to an exemplary image display and a surgical field according to one embodiment of the present disclosure.

FIG. 2A illustrates a block diagram of a user U (e.g., a surgeon or a proctor) relative to an image display 151 (e.g., the image display system 20 shown in FIG. 1A) and a surgical field 155. The user (and his or her eyes) exists in a first 3D coordinate frame 160, the image display 151 includes a second 3D coordinate frame 165, and the surgical field exists in a third 3D coordinate frame 170. Each coordinate frame 160, 165, 170 includes different dimensions and properties from the others. As the user shifts his or her gaze in the first frame 160 relative to the image display 151 in the second frame 165, the embodiments disclosed herein can translate that eye motion into a control signal to correspondingly influence the teleoperational medical system 10 and/or a surgical instrument in the second frame 165 of the display and/or the third frame 170 of the surgical field.

In one aspect, the eye-gaze tracking and observation of other eye characteristics can be used to communicate with and/or influence the behavior of the teleoperational medical system 10 as a whole. For example, the eye characteristics and dynamics observed by the eye tracking unit 24 shown in FIG. 1A may be used for surgeon recognition and log-in (e.g., in a manner similar to retinal scans). In some instances, the eye gaze of the user can be used to better calibrate the 3D positions of surgical instruments in space (e.g., in the third coordinate frame 170) and account for the possible inaccuracies of the telerobotic arm kinematic chain. In some embodiments, a user interface (e.g., a menu) may be overlaid upon the image of the surgical field shown on the image display. In some instances, the eye gaze of the user in the first coordinate frame 160 may be used to determine a viewing location on the image display 151 in the second coordinate frame 165, and can identify a user's selection among user selectable options of the user interface corresponding to the determined viewing location. In some instances, the 3D position of the user's gaze may be used to quantify if the user is seeing stereo or not based on the observed dynamics between the two eyes.

In another aspect, real-time eye-gaze tracking can be used to activate, deactivate, and otherwise control distinct surgical instruments that are coupled to the teleoperational medical system 10 such as, by way of non-limiting example, imaging devices and/or energy delivery devices. For example, the system 10 may be configured to activate a surgical instrument if the control system (e.g., a processor) determines that the viewing location matches the position of the surgical instrument for a predetermined length of time.

FIG. 2B illustrates a flowchart 180 describing an exemplary method of using the eye tracking unit to control and affect the teleoperational medical system 100 and/or any associated surgical instruments. Any of the method processes described herein may be implemented, at least in part, in the form of executable code stored on non-transient, tangible, machine readable media that may be run by one or more processors. At process 182, the user U, in the first coordinate frame 160 shown in FIG. 2A, gazes at a particular 3D position in the image display 151, which is in the second coordinate frame 165. At process 184, the left and right eye trackers of the eye tracking unit (e.g., the eye tracking unit 24 shown in FIG. 1A) observe and measure an eye characteristic (e.g., a characteristic reflective of eye gaze) of the user U. In some embodiments, the eye trackers measure the eye gazes of each eye of the user relative to the second coordinate frame 165 of the image display 151. At process 186, the control system (e.g., the control system 22 shown in FIG. 1A) uses the measured eye gaze data from the eye trackers to determine the 3D location on the image display 151 (within the second coordinate frame 165) at which the user's eyes are directed. In some embodiments, the control system may determine the viewed location by tracking incident angles of the light received by the eye trackers from reflections off the eyes. In some embodiments, the processor 206 may initially perform a calibration process (e.g., the calibration process 302 described in FIG. 4A) to determine baseline incident angles as the user views target indicia that are displayed at known locations on the image display 151, and generate a functional relationship between the detected angles and the viewed locations on the image display 151. The control system can then track the incident angles as the user views other locations on the image display 151 and use the generated functional relationship to determine (e.g., extrapolate from the calibrated angles and locations) the corresponding viewed locations.

At process 188, the control system determines whether one of the displayed indicia (e.g., a menu option) on the image display 151 is being looked at by the user in a way that satisfies a defined condition for selection of that indicia. If so, at process 190, the user's selection of the indicia causes the control system to initiate the function corresponding to the displayed indicia. For example, in some embodiments, the user's gaze may indicate the selection of an indicia associated with logging on to the teleoperational medical system 100, or with the illumination of the image display 151, or with various other system settings.

If not, at process 192, the control system co-registers the viewed 3D location in the second reference frame 165 to the corresponding 3D location in the surgical field 155 in the third coordinate frame 170. At process 194, the control system determines whether the user is looking at the surgical field in a way that satisfies a defined condition for manipulating an imaging device or other surgical instrument. If so, at process 196, the user's gaze upon a particular area of the surgical field or a particular instrument within the surgical field causes the control system to affect the relevant instrument in a fashion corresponding to the characteristics of the user's gaze. For example, in some embodiments, as mentioned above, if the user gazes at a particular region of the surgical field 155, the imaging device may "follow" the user's gaze and re-center its field of view (e.g., to position the center of its field of view at the user's gaze point). In other embodiments, if the user gazes at a particular surgical instrument for a predefined length of time, the surgical instrument may be activated. If not, at process 198, the eye trackers continue to evaluate the user's gaze for possible instructions.

There are a number of methods for measuring eye movement and gaze direction. In one method described herein, an infrared (IR) light emitter emits IR light toward a user's eye. The IR light is reflected from the user's retinas (through the pupils) back to an IR unit (e.g., an IR camera or other imaging device), and the amount of reflected IR light is based on the direction of the person's gaze relative to the emitter. In some embodiments, the user's gaze point in 3D space may be determined once the reflected IR light reaches a particular threshold for a certain amount of time. Small lapses in gaze can be interpreted as blinks and are typically ignored. Other eye tracking methods use video images from which the eye position is extracted, use search coils, or are based on electrooculograms.

Figure 3A:
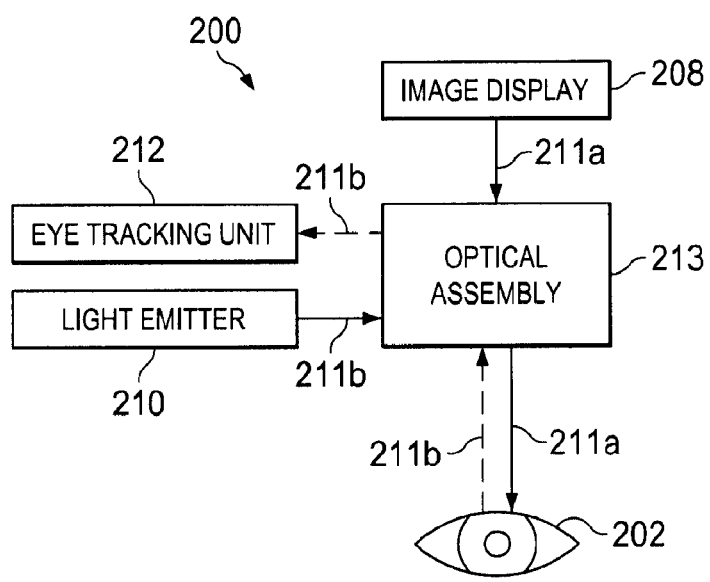

FIG. 3A schematically illustrates an eye tracking system 220 for measuring eye characteristics of the user such as eye position and eye movement to determine his or her gaze point (e.g., "where a user is looking") or the motion of the eye relative to the head. The eye tracking system 200 comprises an image display 208, at least one light emitter 210, an eye tracking unit 212, and an optical assembly 213. One or more eye tracking systems 200 can be integrated in surgeon's console 120. The optical assembly 213 is positioned in the light transmission path between the eye 202 and the light emitter 210, the eye tracking detector 212, and the image display 208. The optical assembly 213 directs eye tracking light (e.g., IR light) from the light emitter 210 to the eye 202, the visible light from the image display 208 to the eye 202, and the reflected eye tracking light (e.g., the IR light) from the eye 202 to the eye tracking detector 212. In this embodiment, the emitted eye tracking light, the reflected eye tracking light, and the visible light share the optical path between the eye 202 and the optical assembly 213. As described in greater detail in FIGS. 3B, 3C, and 3D, the eye tracking unit may be a stereo imaging device employing two or more cameras or other imaging devices or employing a single stereo-capture imaging device. Each eye tracking system 200 can be used to independently track either the surgeon's left eye or right eye. For example, if the optical assembly 213 is used to direct light to the surgeon's left eye (e.g., an eye 202a shown in FIG. 3B), the eye tracking system 200 is configured to detect characteristics indicative of left eye gaze. If the optical assembly 213 is used to direct light to the surgeon's right eye (e.g., the eye 202b shown in FIG. 3B), the eye tracking system 200 is configured to detect characteristics indicative of right eye gaze. As described in greater detail in FIG. 3B, the eye tracking system 200 can be coupled with one or more processors for processing the eye characteristic data (e.g., pupillary position data or corneal reflection data) of the eye 202 tracked by the eye tracking detector 212.

As shown in FIG. 3A, visible light 211a emitted from the image display 208 is directed by the optical assembly 213 towards the surgeon's eye 202. The eye tracking light (e.g. IR light) 211b emitted by the light emitter 210 is directed by the optical assembly 213 towards the surgeon's eye, and is reflected by the surgeon's eye 202 back towards the optical assembly 213. The optical assembly 213 directs the reflected eye tracking light from the surgeon's eye 202 towards the eye tracking unit 212.

In some embodiments, the optical assembly 213 includes one or more mirrors arranged to reflect both the visible light and the eye tracking light. In alternative embodiments, the optical assembly 213 may include a beam splitter or other optical filtering element that reflects some light beams while transmitting others. For example as described in FIG. 3C, the optical assembly can include a dichroic element (e.g., a filter or a mirror) configured to selectively pass light in a particular wavelength range, such as IR light, while reflecting the light outside that particular wavelength range, such as visible light. The optical assembly 213 may also include any other suitable number and arrangement of mirrors and/or other optical devices, such as, by way of non-limiting example, a dichroic mirror (e.g., a partially reflecting mirror that is partially reflective and partially transparent), a reflector having a dichroic optical coating, a dichroic mirrored prism, birefringent materials, and/or polarizing beam splitters. The optical assembly 213 allows the components within the eye tracking system 200 to have a greater variety of possible arrangements because the mirrors and/or filters of the optical assembly 213 may effectively "hide" the eye tracking unit 212 from the surgeon's sight even though the light 211b from the eye tracking unit 212 at least partially shares the same optical path as the visible light from the image display 208.

FIG. 3B is a diagram illustrating an eye tracking system 220 according to one embodiment of the present disclosure. The eye tracking system 220 may be used by the teleoperational medical system 10 of FIGS. 1A, 1B, and 1C. For example, the eye tracking system 220 can be partially or wholly included in the stereo viewer 126 at the surgeon's console 120 according to some embodiments of the present disclosure. The eye tracking system 220 includes left and right eyepieces 125a and 125b, the optical assembly 235 comprising left and right eye mirror sets 204a and 204b, left and right eye image displays 208a and 208b, left and right eye light emitters 210a and 210b, and left and right eye tracking units 212a and 212b. In the pictured embodiment, the eye tracking system 220 includes a left eye processor 214a, a right eye processor 214b, and an integrator 216.

The left and right eyepieces 125a, 125b of the system 220 may be components of the surgeon's console 120 (see FIG. 1C). The left and right eyepieces 125a, 125b include lenses, and the surgeon may view the left and right image displays 208a, 208b through the left and right eyepieces 125a, 125b with the surgeon's left and right eyes, respectively. The lenses may focus light from (e.g., emitted or reflected from) a light source (e.g., the light emitters 210a, 210b and/or the image displays 208a, 208b) towards a detector (such as the eyes 202a, 202b). The lenses may include objective lens that gathers light from the target and focuses the light beam to produce a real image. In some embodiments, the distance between the left and right eye pieces 125a, 125b are adjustable to accommodate different interpupillary distances of different users. In some embodiments, the left and right eye pieces 125a, 125b may be adjusted independently based on the need of the surgeon's left and right eye vision, respectively. In some embodiments, the left and right eye pieces 125a, 125b may include suitable optical coatings configured to minimize reflection and maximize transmission of light from the light emitters and/or left and right eye image displays 208a, 208b.

The left eye and right eye light emitters 210a, 210b emit light 211b to illuminate the surgeon's left eye and right eye, respectively, and the reflected light can be captured by the left and right eye tracking units 212a, 212b, respectively, to track gaze points for the left eye and right eye, respectively. In some embodiments, the left and right light emitters 210a and 210b may be infrared (IR) light emitters, such as IR light emitting diodes (IR LEDs). In some embodiments, there may be more than one light emitter for each eye (e.g., two light emitters for each eye). The multiple light emitters for each eye may be spaced apart by a predetermined distance so that the light emitted from each light emitter appears as separate reflections in a single eye. In some embodiments, the one or more left eye light emitters 210a may be integrated together with the left eye tracking units 212a, and the one or more right eye light emitters 210b may be integrated together with the right eye tracking units 212b. Various embodiments may include any number of tracking units for each eye. Some embodiments may include an unequal number of tracking units for the left eye and the right eye.

The left eye tracking units 212a can be used for tracking the gaze point of the surgeon's left eye, and the right eye tracking units 212b may be used for tracking the gaze point of the surgeon's right eye. As shown in FIG. 3B, each of the eye tracking units 212a, 212b is a three-dimensional imaging system including two eye tracking cameras for stereo eye-tracking. Each eye tracking unit may be used for tracking pupil position and corneal reflection for a respective eye of the surgeon. For example, in the pictured embodiment, two left eye tracking camera 212a1, 212a2 are used for tracking the pupil's position and corneal reflection of the surgeon's left eye. Similarly, in the pictured embodiment, two right eye tracking camera 212b1, 212b2 are used for tracking the pupil's position and corneal reflection of the surgeon's right eye. The multiple eye tracking units for each eye are positioned to be spaced apart from each other by a predetermined distance so that stereo images of each pupil's position and corneal reflection may be independently tracked by the more than one eye tracking unit, and a 3D location of each pupil's position and corneal reflection may be calculated based on the collected data from the independent eye tracking units for each eye. In alternative embodiments, each of the eye tracking units may include a single imaging device, including for example, a stereo camera, or may include more than two imaging devices.

In some embodiments, eye tracking units 212a and 212b are charged coupled device (CCD) cameras. In some embodiments, the eye tracking units 212a and 212b are IR cameras that are sensitive to IR light and can capture the infrared light emitted from IR light emitters. In some embodiments, the eye tracking units 212a and 212b may include a high zoom lens to provide images having higher magnification of the eyes (e.g., the pupils).

In some embodiments, the eye tracking units 212a, 212b and the light emitters 210a, 210b are placed at the base of left eye and right eye image displays 208a, 208b, respectively. In some embodiments, the eye tracking units 212a, 212b may be located in the stereo image viewer system 126 shown in FIG. 1C. The light emitters 210a and 210b may be integrated together with the left and right eye tracking units 212a and 212b, respectively. Typically, the user will position his or her left and right eyes to directly face the left eye and right eye image displays 125a, 125b, respectively. Thus, with this arrangement, each eye tracking unit 212a, 212b is positioned to directly face the eye to be tracked. In particular, the left and right eye tracking units 212a, 212b are positioned to directly face the left eye and the right eye, respectively. The configuration disclosed herein may improve the convenience and accuracy of the eye tracking process because this configuration eliminates the need for external tracking devices, such as eye glasses. In addition, as described above, conventional eye gaze tracking devices may be located near the eyepieces, thereby creating interference when the surgeon is looking into the eyepieces. For example, the edges of the eye gaze tracking device may appear in the surgeon's vision, potentially distracting the surgeon or partially obscuring his view of the surgical field. Thus, the current configuration may improve the surgeon's experience in using the eye tracking technology by eliminating any unnecessary interference images within the surgeon's vision.

In the pictured embodiment and with reference to FIG. 2A, the processors 214a, 214b are coupled to the left and right eye tracking units 212a, 212b, respectively, and are configured to calculate the 3D location of the surgeon's gaze point with respect to the second coordinate frame 165 of the image display 151 (e.g., displays 208a, 208b) and translate that 3D position into the corresponding 3D position of the third coordinate system 170 of the surgical field 155 (shown in FIG. 2A). For example, the gaze points captured by the left and right eye tracking units 212a, 212b can be rectified, and the disparity between the gaze points of the surgeon's left and right eyes can be determined. The 3D location of the surgeon's gaze point can then be calculated using the distance between the left and right eye tracking units 212a, 212b, the parameters related to the focal length of each of the left and right eye tracking units 212a, 212b, and the determined disparity.

A 3D stereo image of the surgical field may be perceived by the surgeon via the eye tracking system 220. In some embodiments, the endoscope 112 located at the teleoperational assembly 100 can be manipulated to capture images of the surgical field 155 during a surgery (shown in FIG. 2A), and these images can be shown on the left and right image displays 208a, 208b. In some embodiments, the image displays 208a, 208b are the same as the image display 151 shown in FIG. 2A. In some embodiments, the endoscope 112 comprises a stereoscopic camera. The images captured by the endoscope 112 may then be processed by the processors 214a, 214b to generate left and right stereo images, respectively. The generated left and right stereo images may be shown on left and right image displays 208a and 208b, respectively. In particular, the left eye image display 208a is communicatively coupled to the endoscope 112, and is configured to display a left eye stereo image of a surgical site during a surgery. Similarly, the right eye image display 208b is coupled to stereoscopic camera 112 and is configured to display a right eye stereo image of the surgical site. The left eye and right eye stereo images are captured by stereoscopic camera 112 and processed for left and right eye vision respectively. The left eye and right eye image displays 208a, 208b may be 2D or 3D display screens. In some embodiments, the left eye and right-eye image displays 208a, 208b are liquid crystal display (LCD) screens. In some instances, the image displays 208a, 208b may be presented simultaneously on multiple display screens or devices (e.g., an external screen or mobile device).

As mentioned above, the eye tracking system 220 includes a left eye processor 214a, a right eye processor 214b, and an integrator 216. The processors 214a, 214b and the integrator 216 are configured to process gaze point data received from the eye tracking units 212a, 212b to determine a viewing location on the image displays 208a, 208b at which the gaze point of the user is directed, and to control at least one function of the teleoperational medical system 10 based on the determined viewing location. In particular, the processors 214a, 214b may process pupillary position and corneal reflection point data received by left eye and right eye tracking units 212a, 212b. In some embodiments, the pupillary position and corneal reflection point data received by each eye tracking unit may be processed by processors 214a and 214b to determine the 3D location of the pupil's position and corneal reflection. The integrator 216 may be used to integrate the pupillary position and corneal reflection data received from each eye to form a 3D gaze point or location of the surgeon during a surgery.

In some embodiments, the functions of the left eye and right eye processors (and/or the integrator) may performed by a single processor. In some embodiments, the integrator 216 integrates the information received by both processors 214a, 214b to determine and process the eye gaze locations of the user. In some embodiments, the processors 214a, 214b and/or the integrator 216 may be located elsewhere within the teleoperational system 10 (e.g., within the vision cart 140 as part of the central electronic data processing unit 142, at the teleoperational assembly 100, and/or within the surgeon's console 120). In some embodiments, the processors 214a, 214b and/or the integrator 216 can also be coupled to a memory to store the gaze point measurement, registration, and calibration data. In some embodiments, the processors 214a, 214b and/or the integrator 216 may be used to calculate the 2D location of the surgeon's gaze point. As described in further detail below, in some embodiments, the head motion of the surgeon may be compensated for when determining the 3D location of the pupil's position and corneal reflection.

In some embodiments, the calculated 2D or 3D location of the surgeon's gaze point can be displayed in any of a variety of suitable representations, such as dots, flags, or vectors showing the changes of the surgeon's gaze point. The surgeon's gaze point can be displayed in combination with the image of the surgical field 155 on the left and right image displays 208a, 208b. In some embodiments, the eye tracking system 220 may also be used in the surgeon's console 120 integrated with a simulation module, e.g., a da Vinci® Skills Simulator™, where virtual images can be shown on the left and right image displays 208a and 208b.

The optical assembly 235 is arranged relative to the eyes 202, the light emitters 210, the eye tracking units 212, and the image displays 208 to direct the IR light from the light emitters 210 to the eyes 202, the visible light from the image displays 208 to the eyes 202, and the reflected IR light (emitted from the light emitters 210) from the eyes 202 to the eye tracking units 212. In particular, each of the left and right mirror sets 204a, 204b of the optical assembly 235 comprises a plurality of mirrors arranged to reflect the IR light from the left and right light emitters 210a, 210b, respectively, into the left and right eyes of the surgeon, respectively, and to reflect IR light from the left and right eyes into the left and right eye tracking units, 212a, 212b, respectively.

Thus, the left eye mirror set 204a includes a set of mirrors that are arranged to provide optical communication between the surgeon's left eye, the left eye tracking units 212a, and the left eye light emitter 210a. For example, the mirrors 204a may be arranged, as shown in FIG. 3B, so that the left eye portion of the stereo image shown on the left eye image display 208a can be directed via visible light 211a into the surgeon's left eye to be seen by the surgeon. The left eye mirror set 204a may also allow the IR light 211b emitted from left eye light emitter 210a to be directed onto the surgeon's left eye. The reflected IR light 211b from the surgeon's left eye may be directed by left eye mirror set 204a to the left eye tracking units 212a, thereby enabling the left eye tracking unit 212a to track the reflected IR light to determine the 3D location of the gaze point of the surgeon's left eye.

Similarly, the right eye mirror set 204b includes a set of mirrors that are arranged to provide optical communication between the surgeon's right eye, the right eye tracking units 212b, and the right eye light emitter 210b. For example, the mirrors 204b may be arranged, as shown in FIG. 3B, so that the right eye portion of the stereo image shown on the right eye image display 208b can be directed with visible light 211a to the surgeon's right eye to be seen by the surgeon. The right eye mirror set 204b may also allow the IR light 211b emitted from right eye light emitter 210b to be directed onto the surgeon's right eye. The reflected IR light 211b from the surgeon's right eye may be directed by the right eye mirror set 204b to right eye tracking units 212b, thereby enabling the right eye tracking unit 212b to track the reflected IR light to determine the 3D location of the gaze point of the surgeon's right eye. In FIG. 3B, the path of the emitted and reflected IR light 211b shares an optical path with the visible light 211a between the display 208a and the eye 202a and between the display 208b and the eye 202b.

As mentioned above, in some embodiments, the left eye and right eye tracking units 212a, 212b may also be used to track 3D head motions of the surgeon (e.g., in the first coordinate frame 160 shown in FIG. 2A). In some embodiments, the tracking units 212a, 212b track the 3D motion of the surgeon's head by monitoring a fixed reference point on the surgeon's head (e.g., including the face). Because the reference point does not have continuously synchronized motion with the surgeon's eye gaze point, the reference point may be used to estimate the surgeon's head position and orientation. The reference point may comprise any of a variety of anatomical landmarks or features on the surgeon's head. For example, the reference point may include a head feature such as eyelid curvatures, corners of the eyes, irises, and/or eyebrows. In some examples, the head feature that is used as the reference point may be segmented and tracked. For example, in one embodiment, the corner of the eye may be detected and located by the intersection of two splines of the eye. When two stereo units (e.g., the left eye and right eye tracking units 212a, 212b) are used, the head feature may be tracked in 3D space. The interpupillary distance between the surgeon's left and right eyes is assumed to be constant, and used by the processor as a constant factor in its calculations. When the surgeon moves his or her head or face without shifting his or her gaze point, the surgeon's pupils remain stationary relative to the eye tracking units 212a, 212b. Accordingly, the reference point on the head moves while the surgeon's pupils remain fixed relative to the eye tracking units 212a, 212b. Therefore, there is a relative motion between the left and right pupils and the reference point on the face/head. This relative motion may be tracked and monitored by the left eye and right eye tracking units 212a and 212b to calculate appropriate compensation values. These compensation values may be used to compensate for the tracked 3D head motions in determining the 3D location of the gaze point of each of the surgeon's eyes.

FIG. 3C is a diagram illustrating an eye tracking system 250 including an optical assembly 255 that operates as a beam splitter. The eye tracking system 250 is an exemplary embodiment of the eye tracking system 200 of FIG. 3A. The eye tracking system 250 can be partially or wholly included in the stereo image viewer system 126 on the surgeon's console 120 according to various embodiments of the present disclosure. The eye tracking system 250 includes the left eye tracking units 212a (with eye tracking cameras 212a1, 212a2), the right eye tracking units 212b (with eye tracking cameras 212b1, 212b2), the left eye light emitter 210a, the right eye light emitter 210b, the left eye image display 208a, the right eye image display 208b, the left eye processor 214a, the left eye processor 214b, and the integrator 216. However, in the eye tracking system 250 shown in FIG. 3C, these components are arranged in a different configuration than in the eye tracking system 220. In the eye tracking system 220 shown in FIG. 3B, the eye tracking units 212a, 212b and the light emitters 210a, 210b are located beneath the image displays 208a, 208b (relative to the user). The optical assembly 235 is positioned between the image displays 208a, 208b and the eyepieces 125a, 125b. In contrast, in the eye tracking system 250 shown in FIG. 3C, the left eye and right eye tracking units 212a, 212b are located in front of the image displays 208a, 208b in an area or space between the left eye and right eye image displays 208a, 208b and the optical assembly 255. The optical assembly 255 comprises the left eye mirror set 204a and the right eye mirror set 204b. The left eye mirror set 204a comprises a first optical element 256 and a second optical element 257. The right eye mirror set 204b comprises a third optical element 258 and a fourth optical element 259. The optical elements 256, 257, 258, and 259 can be any of a variety of light-transmitting and/or light-reflecting optical devices, including without limitation, mirrors, filters, and prisms. Although two processors 214a, 214b are shown in FIG. 3C, one with ordinary skill in the art would understand that any number of processors may be arranged in any suitable topology.

In some embodiments, the optical assembly 255 includes at least one mirror set including a beam splitter, such as, by way of nonlimiting example, a dichroic mirror or a dichroic filter. The beam splitter may comprise any device capable of both transmission and reflection of light within distinct wavelength ranges. For example, as shown in FIG. 3C, the second optical element 257 of the left eye mirror set 204a includes a left beam splitter 257 that allows IR light 211b to pass through while reflecting visible light 211a, such as the visible light emitted from the left eye stereo image display 208a. Thus, the IR light 211b emitted from the left eye light emitter 210a can pass through the left beam splitter 257 to illuminate the left eye, and the reflected IR light 112b from the surgeon's left eye 202a can also pass through the left beam splitter 257 to be captured by left eye tracking unit 212a. At the same time, the visible light 211a emitted from left eye image display 208a can be directed by the optical elements 256 and 257 of mirror set 204a to be seen by the surgeon's left eye 202a. In some embodiments, the left beam splitter 257 comprises a dichroic mirror.

Similarly, the third optical element 258 of the right eye mirror set 204b includes a right beam splitter that allows IR light 211b to pass through while reflecting visible light 211a, such as the visible light emitted from the right eye stereo image display 208b. Thus, the IR light 211b emitted from the right eye light emitter 210b can pass through the right beam splitter 258 to illuminate the right eye, and the reflected IR light 211b from the surgeon's right eye 202b can also pass through the right beam splitter 258 to be captured by right eye tracking unit 212b. At the same time, the visible light 211a emitted from right eye image display 208b can be directed by the mirror set 204b (and the beam splitter 258) to be seen by the surgeon's right eye 202b. In some embodiments, the right beam splitter 258 comprises a dichroic mirror.

The inclusion of beam splitters 257, 258 in the optical assembly 255 allows for a configuration in which the eye tracking units 212a, 212b share at least part of the optical path for the displayed images originating from the image displays 208a, 208b without being visible to the surgeon (e.g., in the image displays 208a, 208b). In other words, the reflected IR light 211b shares a portion of the optical path of visible light 211a, namely the portion of the optical path between the eye and the respective beam splitter (e.g., between eye 202a and beam splitter 257 and between eye 202b and beam splitter 258). As shown in FIG. 3C, the left eye and right eye tracking units 212a, 212b are positioned behind the beam splitters 203a, 203b and directly facing the surgeon's eyes. This configuration allows the eye tracking units 212a, 212b to capture information from the surgeon's left and right eyes 202a, 202b, respectively, without obstructing the visible light path and without having any optical reflection paths affect the image displays 208a, 208b (e.g., without the image displays 208a, 208b receiving any reflected IR light from the surgeon's eyes). In contrast, as shown in FIG. 3B, the reflected IR light (shown by dashed line arrows) from the surgeon's eyes 202a, 202b is reflected back toward the image displays 208a, 208b to be received by the eye tracking units 212a, 212b.

In some instances, the incorporation of a beam splitter (e.g., the beam splitter 257, 258) in the optical assembly 255 of the eye tracking system 250 allows the light 211b from eye tracking units 212a, 212b to share at least part of the optical path of the visible light 211a from the displayed images without having the eye tracking units 212a, 212b visible to the surgeon. In some instances, the surgeon may be less distracted by interference images and more focused on the current procedure because this configuration may eliminate interference images from the eye tracking units in the surgeon's image displays 208a, 208b. In addition, the configuration shown in FIG. 3C may also provide more flexibility or compactness for the design and manufacturing of the eye tracking system 250. The configuration of system 250 may create a clearer view of the display (without the eye tracking unit visible) while accommodating minimized space and design constraints.

Figure 3D:
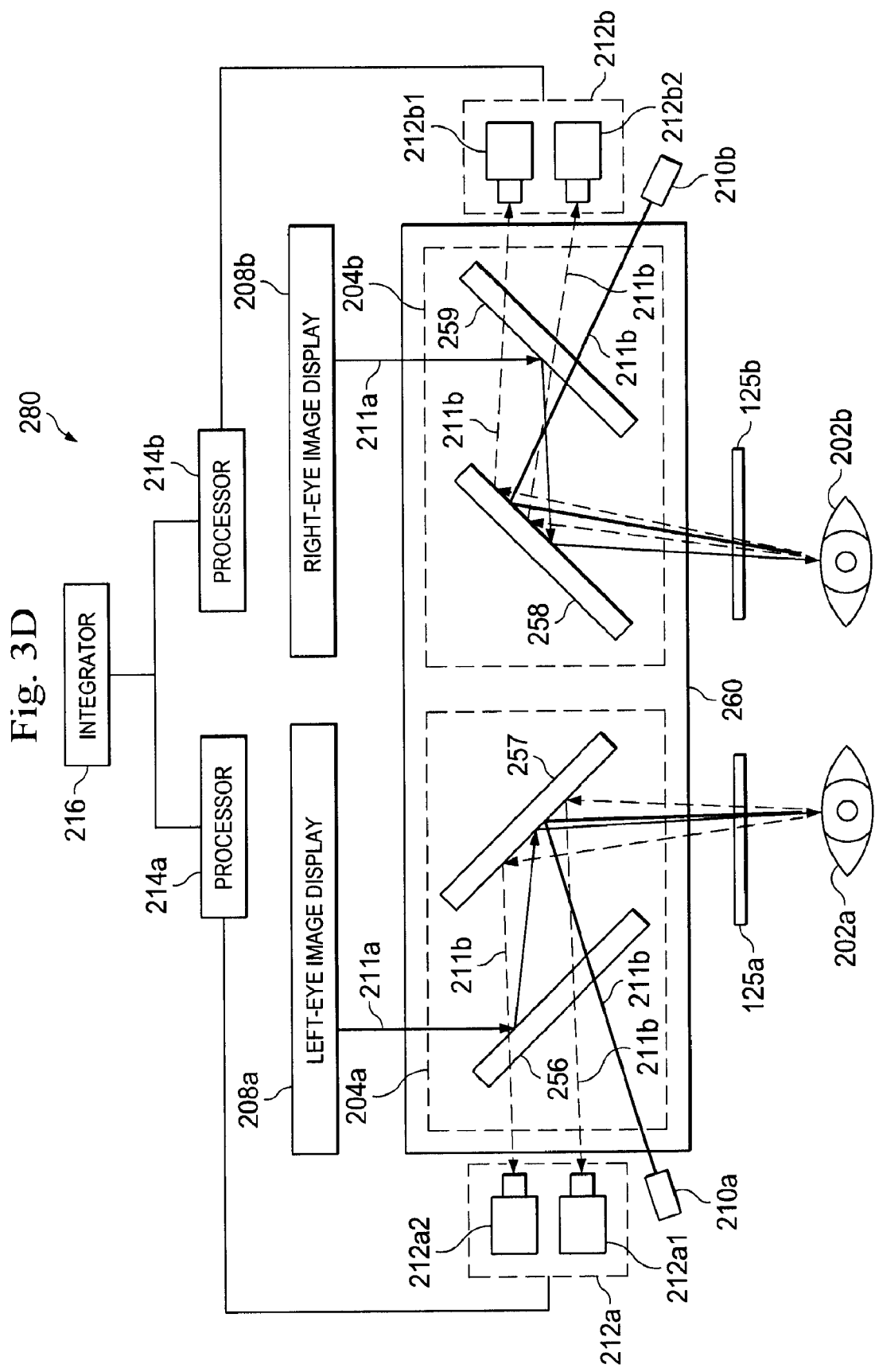

FIG. 3D is a diagram illustrating an exemplary eye tracking system 280 including an optical assembly 260 that operates as a beam splitter according to one embodiment of the present disclosure. The eye tracking system 280 is another exemplary embodiment of the eye tracking system 200 shown in FIG. 3A. The eye tracking system 280 may be partially or wholly included in stereo image viewer system 126 on the surgeon's console 120 according to some embodiments of the present disclosure. The eye tracking system 280 includes the left eye tracking units 212a (with eye tracking cameras 212a1, 212a2), the right eye tracking units 212b (with eye tracking cameras 212b1, 212b2), the left eye light emitter 210a, the right eye light emitter 210b, the left eye image display 208a, the right eye image display 208b, the left eye processor 214a, the left eye processor 214b, and the integrator 216. In the eye tracking system 280 shown in FIG. 3D, these components are arranged in a different configuration than in the eye tracking system 250. In particular, in the eye tracking system 250 shown in FIG. 3C, the eye tracking units 212a, 212b and the light emitters 210a, 210b are positioned between the image displays 208a, 208b and the optical assembly 255. In contrast, in the eye tracking system 280 shown in FIG. 3D, the eye tracking units 212a, 212b and the light emitters 210a, 210b are located adjacent to (e.g., lateral to) the optical assembly 260 (or rotated approximately 90° with respect to the eyes). In the pictured embodiment of FIG. 3D, the space between the optical assembly 260 and the image displays 208a, 208b is unoccupied, thereby providing an unobstructed optical path between the image displays 208a, 208b and the optical assembly 260.

Like the optical assembly 255 shown in FIG. 3C, the optical assembly 260 of the eye tracking system 280 includes two optical elements that act as beam splitters. In the optical assembly 260 shown in FIG. 3D, the first and fourth optical elements 256 and 259 act as beam splitters. In particular, the first optical element 256 of the left eye mirror set 204a includes a left beam splitter, and the fourth optical element 9 of the right eye mirror set 204b includes a right beam splitter. As shown in FIG. 3D, the left beam splitter 256 of the left eye mirror set 204a transmits IR light 211b through while reflecting visible light 211a, such as the visible light emitted from the left eye stereo image display 208a. Thus, the IR light 211b emitted from the left eye light emitter 210a can pass through the left beam splitter 256 to illuminate the left eye, and the reflected IR light from the surgeon's left eye 202a can also pass through the left beam splitter 256 to be captured by left eye tracking unit 212a. At the same time, the visible light emitted from left eye image display 208a can be directed by the mirror set 204a (including the beam splitter 256) to be seen by the surgeon's left eye 202a. In some embodiments, the left beam splitter 6 comprises a dichroic mirror.

Similarly, the right beam splitter 259 of the right eye mirror set 204b transmits IR light 211b through while reflecting visible light 211a, such as the visible light emitted from the right eye stereo image display 208b. Thus, the IR light 211b emitted from the right eye light emitter 210b can pass through the right beam splitter 259 to illuminate the right eye, and the reflected IR light 211b from the surgeon's right eye 202b can also pass through the right beam splitter 259 to be captured by right eye tracking unit 212b. At the same time, the visible light 211a emitted from right eye image display 208b can be directed by the mirror set 204b (and the beam splitter 259) to be seen by the surgeon's right eye 202b. In some embodiments, the right beam splitter 259 comprises a dichroic mirror.

The inclusion of the beam splitters 257, 259 in the optical assembly 260 allows for a configuration in which the light 211b from eye tracking units 212a, 212b share at least part of the optical path for the displayed images originating from the image displays 208a, 208b without the eye tracking units being visible to the surgeon. In particular, as shown in FIG. 3D, the left eye and right eye tracking units 212a, 212b are positioned behind the beam splitters 257, 259 and at an angle (e.g., 90°) to the surgeon's eyes. This configuration allows the eye tracking units 212a, 212b to capture information from the surgeon's left and right eyes, respectively, without obstructing the path of the visible light from the displays and without having any optical reflection paths affect the image displays 208a, 208b (e.g., without the image displays 208a, 208b receiving any reflected IR light from the surgeon's eyes).

In some instances, the incorporation of a beam splitter (e.g., the beam splitter 256, in the optical assembly 260 of the eye tracking system 280 allows the light 211b from eye tracking units 212a, 212b to share at least part of the optical path of the visible light 211a from the displayed images without having the eye tracking units 212a, 212b visible to the surgeon. In some instances, the surgeon may be less distracted by interference images and more focused on the current procedure because this configuration may eliminate interference images from the eye tracking units in the surgeon's image displays 208a, 208b. In addition, the configuration shown in FIG. 3D may also provide more flexibility or compactness for the design and manufacturing of the eye tracking system 280. The configuration of system 280 may create a clearer view of the display (without the eye tracking unit visible) while accommodating minimized space and design constraints.

It is to be understood that the position of the light emitters 210 (e.g., left eye and right eye light emitters 210a and 210b) is flexible. The position of the eye tracking units 212 (e.g., the left and right eye tracking units 212a and 212b) is also flexible. One of ordinary skill in the art would understand that the light emitter 212 and/or the eye tracking unit 212 can be located at any suitable position relative to the surgeon and the image displays (e.g., on the surgeon's console 120) to minimize interference to the surgeon's vision and to improve the accuracy and efficiency of the eye tracking process.

Figure 4A:
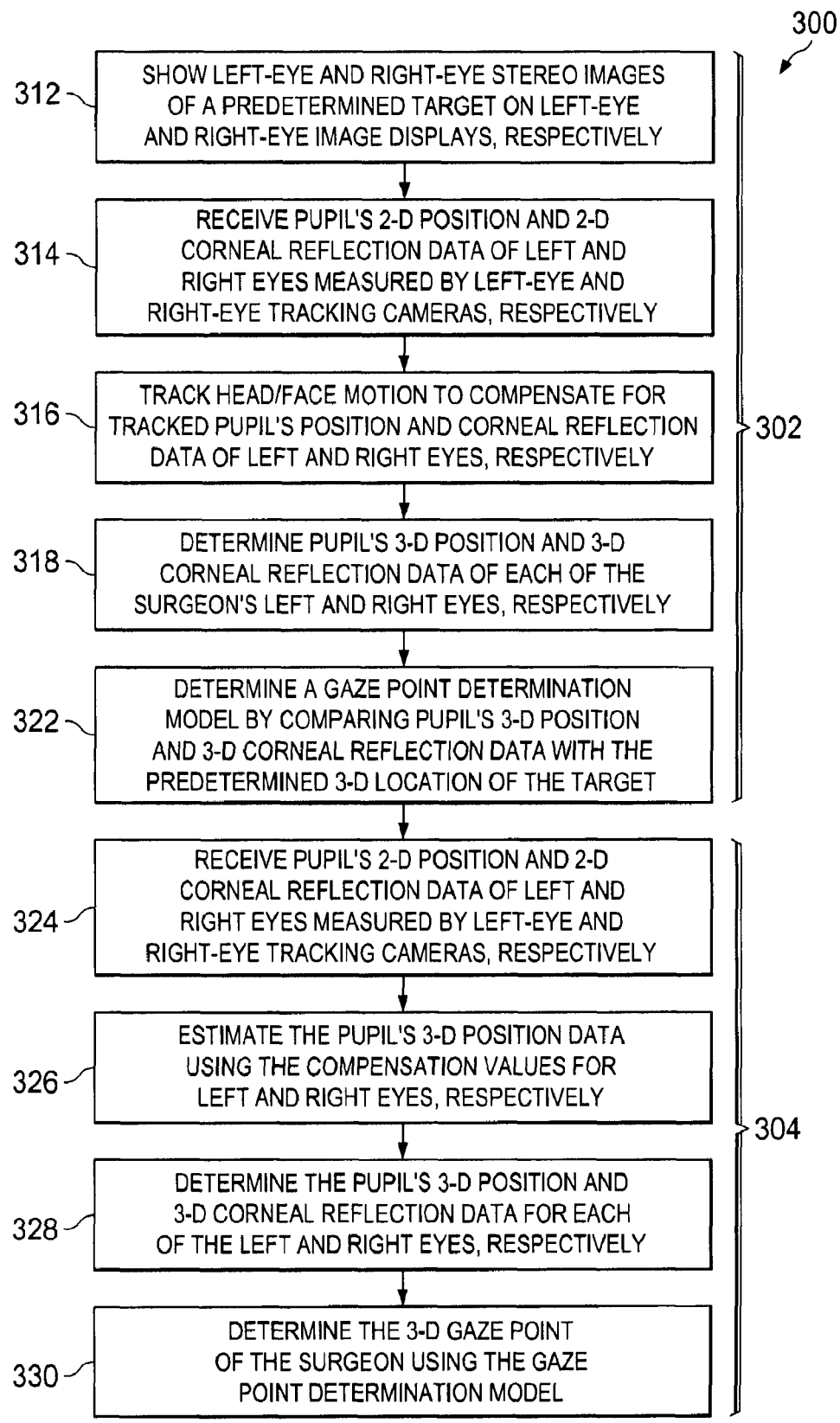
FIG. 4A illustrates a method for determining the surgeon's 3D gaze point using the eye tracking system of FIGS. 3A-3D according to one embodiment of the present disclosure.

FIG. 4A illustrates a method 300 for determining the surgeon's 3D gaze point using the eye tracking systems as shown in FIGS. 3A-3D according to an embodiment of the present disclosure. The method 300 includes two processes: a calibration process 302 and a measurement process 304. In some embodiments, the calibration process 302 is a 3D calibration process, where the surgeon's gaze point in the 3D space is compared with a predetermined target in the 3D space with known 3D location parameters.

The image of the target T shown in the 3D space may be separated into left and right stereo images, and displayed on the left and right image displays 208a, 208b, respectively. The left eye and right eye light emitters 210a, 210b may emit light that can be tracked by the left eye and right eye tracking units 212a, 212b, respectively. The left eye and right eye mirror sets 204a and 204b may be arranged so that the left eye and right eye stereo images of the target displayed on the left eye and right eye image displays 208a and 208b can be reflected and directed into the surgeon's left and right eyes 202a, 202b, respectively. In some embodiments, as shown in FIGS. 3A-3D, the left eye and right eye mirror sets 204a and 204b are arranged so that there is no "crosstalk" or shared optical pathways between the left eye and right eye optical communication. Light, such as IR light 211b, emitted from the light emitters 210a, 210b can also be directed through the left eye and right eye mirror sets 204a, 204b to illuminate the surgeon's left and right eyes 202a, 202b. During the calibration process, the 3D location of the target is predetermined, for example, with known 3D location parameters in the 3D space, so that the measured data may be compared with the predetermined location data of the target subject to determine the compensation values and/or gaze point determination model in the following process.

Figure 4B:
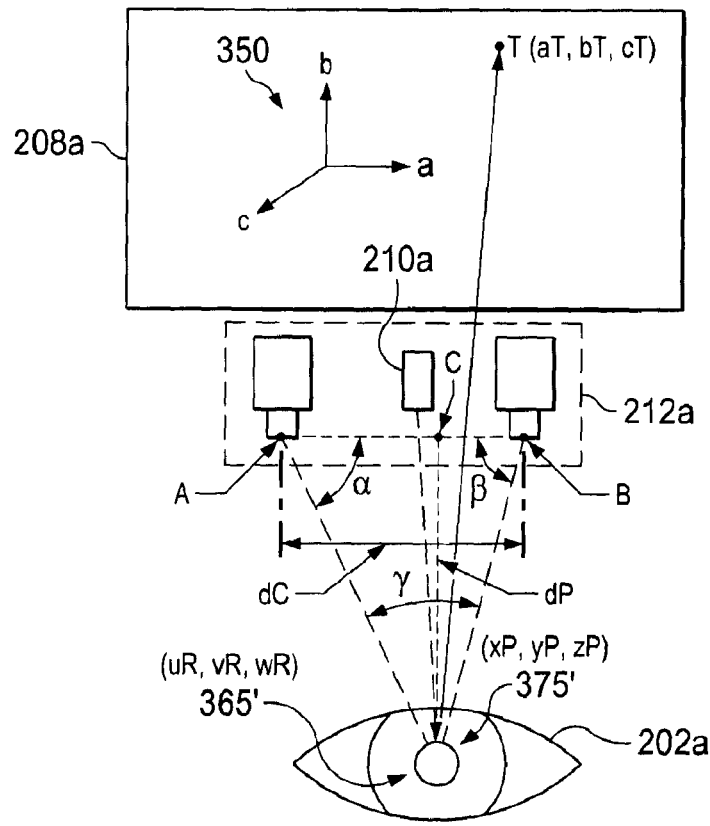
FIG. 4B is a schematic drawing illustrating an example of eye tracking units tracking the corneal reflection and the pupil of the surgeon when a predetermined target T is shown on a display during the calibration process according to one embodiment of the present disclosure.

FIG. 4B illustrates an example of the left eye tracking units 212a tracking the corneal reflection and the pupillary location of the surgeon's left eye 202a when a predetermined target T (having the 3D coordinates aT, bT, cT) is shown on the left eye image display 208a during the calibration process. The calibration process 302 may begin at process 312 by showing a target Tin the 3D space. As shown in FIG. 4B, the target T can be placed in a predetermined 3D coordinate frame 350 with coordinate values of (aT, bT, cT) on the left eye image display 208a. The target T shown on the left eye image display 208a may be a left eye stereo image captured by stereoscopic unit 112 and processed by processor 214a. In other embodiments, the target T may be a virtually created image. The left eye mirror set 204a (not shown) can be situated at any suitable position relative to the left eye tracking units 212a and the surgeon's left eye 202a, as discussed above in relation to FIGS. 3A-3D. It is to be understood that although only one corneal reflection of the surgeon's left eye is shown in FIG. 4B for the sake of simplicity, there may be more than one corneal reflection from the more than one light emitters 210 for each eye 202.

In some examples, the target T may be a surgical tool icon shown in the 3D space 350. The target T may also be a moving target, or a target that may change size dynamically. Alternatively, the target may also be an actual surgical tool in the surgical field, the location of which can be tracked and identified using any suitable tool tracking technology. For example, the calibration process 302 may incorporate features disclosed in U.S. Patent Publication No. 2006/0258938, entitled "Methods and system for performing 3D tool tracking by fusion of sensor and/or camera derived data during minimally invasive robotic surgery," filed on May 16, 2005, which is incorporated herein by reference. During the calibration process 302, the 3D location of the target T is predetermined, for example with known 3D location parameters in the 3D space (e.g., the coordinate values of (aT, bT, cT)), so that the measured data may be compared with the known location parameters of the target T to determine various models in the following steps.

In the pictured embodiment, the calibration process 302 proceeds to process 314 by receiving the pupil's 2D position and 2D corneal reflection data of left and right eyes captured by the left and right eye tracking units 212a and 212b, respectively. In some embodiments, the 2D pupillary position and 2D corneal reflection data may include coordinate values, displacements, and/or angles. In some embodiments, left eye and right eye mirror sets 204a and 204b are arranged as shown in FIGS. 3A-3D, so that the corneal reflections of the surgeon's left and right eyes 202a, 202b can be directed into the left eye and right eye tracking units 212a, 212b, respectively, to be tracked. The tracked 2D data may then be received and processed by the left eye and right eye processors 214a, 214b and/or the integrator 216 to obtain the 3D pupillary position and corneal reflection data of surgeon's left and right eyes 202a, 202b.

Figure 4C:
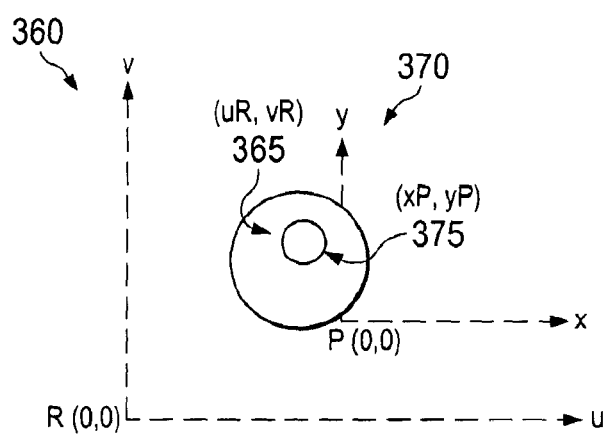
FIG. 4C is a schematic drawing illustrating an example of 2D coordinate frames corresponding to the corneal reflection and the pupillary position of the surgeon according to one embodiment of the present disclosure.

FIG. 4C illustrates a 2D coordinate frame 360 corresponding to the surgeon's cornea, and a 2D coordinate frame 370 corresponding to the surgeon's pupil. As shown in FIG. 4C, when the left eye light emitter 210a emits light toward the surgeon's eye 202a, the light (e.g., IR light) reflects off the surface of a cornea of the surgeon's left eye 202a, and the reflection image becomes a bright region with a corneal reflection center 365 (having the coordinates (uR, vR)) placed in the predetermined 2D coordinate frame 360. In some instances, the corneal reflection data includes tracking information for more than one corneal reflection per eye. The center of the pupil 375 (having the coordinates (xP, yP)) in the predetermined 2D coordinate frame 370 can also be tracked by the left eye tracking units 212a.

The calibration process 302 proceeds to process 316 by tracking the head motion to more accurately determine the pupillary position and corneal reflection data of left and right eyes, respectively. In other words, the head motion data may be used to compensate for the head motion-induced inaccuracies of the pupillary position and corneal reflection data. For example, rotations of the head can be approximated by changes in the head motion data. In some embodiments, as described above in relation to FIG. 3A, a head feature (e.g., a corner of an eye) of the surgeon may be tracked to determine the head motion. In some embodiments, the surgeon may be requested to perform one or more head motions while focusing on a target T in the image displays 208a, 208b to determine the appropriate compensation values and/or compensation model. For example, the surgeon may be requested to move his or her head closer to the eyepieces 125a, 125b while focusing on a predetermined target T on the image displays 208a, 208b. The surgeon may also be requested to move his or her head in a series of motions (e.g., up and down, left and right, in a rotation, and/or further away from the eyepieces) to gather more calibration information.

The left eye and right eye tracking units 212a and 212b may capture the relative motion between the surgeon's pupils and the face/head feature to determine the compensation values related to the face/head motion. In some embodiments, the head motion of the surgeon may also be tracked by one or more sensors mounted on the headrest 130. The calculated 2D or 3D gaze point location may be further adjusted or compensated for based on the tracked head motion of the surgeon. The data collected by the sensors may be combined with the data acquired at process 316 to determine the compensation values. Additional details on using the sensing method to manipulate the headrest may be found, for example, in U.S. Application No. 61/865,996, entitled "ENDOSCOPE CONTROL SYSTEM."

In some embodiments, the compensation values and/or compensation model may be saved in a memory coupled to the processors 214a, 214b and/or the integrator 216 for future measurements or calculations. In some embodiments, the compensation values and/or compensation model of a specific user may be saved in the memory as part of the user's profile data so that the same user does not need to repeat the calibration process when the user logs into the system again.

The calibration process 302 proceeds to process 318 by determining the 3D pupillary position and 3D corneal reflection data of each of the surgeon's left and right eyes 202a, 202b, respectively. In some embodiments, the eye tracking units 212a include stereo cameras, and stereo images including the 2D pupillary position and 2D corneal reflection data can be captured and processed by the processors 214a to calculate a disparity between the multiple stereo images. For example, as shown in FIG. 4B, when the one or more left eye tracking units 212a include a stereo camera that can capture stereo images of the surgeon's left eye 202a, the 2D pupillary position 375 (xP, yP) and 2D corneal reflection data 365 (uR, vR) from each individual left eye tracking unit 212a may be processed to calculate a disparity between the multiple stereo images. In some embodiments, the determined position data may include the 2D pupillary position and 2D corneal reflection data of the surgeon's left eye 202a.

The determined 2D data of each eye may then be combined to estimate the 3D eye gaze location of the surgeon. In some embodiments, the determined position data may include the pupil's 3D position and 3D corneal reflection data. A disparity to depth conversion map may be obtained during the calibration process using this method. The 3D data including depth of the surgeon's pupil (coordinate point zP) and depth of corneal reflection (coordinate point wR) may then be estimated using the disparity. For example, the 3D eye gaze data of the surgeon's left eye 202a may be calculated using the distance between the left eye tracking units 212a, the parameters related to the focal length of each of the left eye tracking units 212a, and the calculated disparity. A disparity to depth conversion map may be obtained during the calibration process using this method. In some embodiments, the surgeon's head motion may also be captured by the left and right eye trackers 204a and 204b.

In some embodiments, the surgeon's pupil may show a vergence (e.g., as indicated by an angle γ shown in FIG. 4B) when looking at a target T with different depths. The depth of the surgeon's pupil and corneal reflection may be estimated by monitoring the vergence (e.g., the angle γ) of each of the surgeon's pupils and forming a conversion chart between the measured interpupillary distance and the depth of the target T in the 3D coordinate frame 350. In some embodiments, the depth of the surgeon's pupil (e.g., zP) and depth of corneal reflection (e.g., wR) may be calculated using a triangulation method as illustrated in FIG. 4B. For example, the distance between the multiple left eye tracking units 212a is set to be a distance dC (e.g., the distance between points A and B in FIG. 4B), and the triangulation angles α and β may be tracked when the surgeon's eye is looking at target T at different locations in 3D coordinate frame 350. In one instance, when the target T is located at different depths, the angles α and β may change accordingly, so that a distance dP (e.g., the distance between point C and the pupil) between the eye tracking units 212a and the pupil can be calculated. The distance value dP can be further used to calculate the 3D pupillary position (e.g., coordinates (xP, yP, zP)). The 3D pupillary position (e.g., coordinates (xP, yP, zP)) and corneal reflection data (e.g., coordinates (uR, vR, wR)) of the surgeon's right eye may be determined in a substantially similar manner as the determination of the surgeon's left eye.

At process 322 of the calibration process 302, the determined 3D pupillary position and 3D corneal reflection data is compared with the predetermined 3D location parameters of the predetermined target T to determine a gaze point determination model. In other words, the gaze point determination model can be formed by determining the relationship between the 3D pupillary position and 3D corneal reflection data and the 3D location of the predetermined target T. In some examples, the determined 3D pupillary position 375' (coordinates (xP, yP, zP)) and the 3D corneal reflection data 365' (coordinates ((uR, vR, wR)) of the surgeon's left eye 202a is compared with the 3D location data T (coordinates (aT, bT, cT)) of the left stereo image of the target T chosen at process 312 to obtain the following relationship or function f:

$(aT, bT, cT) = f(xP, yP, zP, uR, vR, wR)$

In some embodiments, a plurality of calibration targets are used for the calibration processes, and the parameters of the function f may be determined using the pupil's position and corneal reflection data gathered from the plurality of target points during the calibration process. In some examples, methodologies such as least squares optimization, or maximum likelihood estimation may be used to determine the parameters of the function f. In some embodiments, a gaze direction vector for each eye can be formed using the 3D pupillary position and 3D corneal reflection data of each eye and an intersection of each gaze direction vector may be determined to be the surgeon's gaze point. The determined gaze point may then be compared with the 3D location data of the target T to determine the function f. In some embodiments during the calibration process, the error between the 3D location calculated using function f and the actual predetermined location of the target T may be minimized using an optimization method, such as least squares optimization, maximum likelihood estimation. In some embodiments, the gaze point determination model may also be formed using 2D position data of the surgeon's eyes, the 2D location data of the target, and the vergence (e.g., angle γ) of the surgeon's pupils. In some embodiments, the gaze point determination model may also include a matrix showing the conversion from the pupil's 3D position and 3D corneal reflection data to the 3D location of the target T in a coordination system in the 3D space.

Similarly, the 3D pupillary position and 3D corneal reflection data of the surgeon's right eye 202b may be compared with the 3D location data of the right stereo image of the target T chosen at process 312.

In some embodiments, the calibration process 302 may be repeated multiple times, so that the accuracy of the gaze point determination model may be improved until the accuracy satisfies a predetermined system requirement. In some embodiments, after a first gaze point determination model (e.g., function f) is formed, one or more real targets may be used to estimate the accuracy of the first gaze point determination model. For example, by rerunning the mapping optimization using the real target(s), the first gaze point determination model may be updated to form a second gaze point determination model. The accuracy between the first and second models is compared and evaluated, so that a more accurate gaze point determination model may be formed.

After the calibration process 302 is completed, the method 300 proceeds to a measurement process 304. The measurement process 304 may be carried out during a surgery or a training process when the endoscope or stereoscopic camera 112 is capturing an image of a surgical site. In some embodiments, the calibration process 302 and the measurement process 304 may also be conducted in a simulated exercise using a simulation module, for example using a da Vinci® Skills Simulator™ (e.g., that may be integrated with the surgeon's console 120).

The measurement process 304 starts at process 324 by receiving the 2D pupillary position and 2D corneal reflection data of surgeon's left and right eyes 202a, 202b, respectively, when the surgeon is looking at images (e.g., a surgical site or virtual image) displayed on left eye and right eye image displays 208a, 208b. The configuration and method for process 324 may be substantially similar to process 314 of method 300 as previously discussed. In some embodiments, the image of the surgical site may be captured by the endoscope or stereoscopic camera 112 and processed to be separated into left eye and right eye stereo images displayed on the left eye and right eye image displays 208a, 208b, respectively. The 2D pupillary position and 2D corneal reflection data of surgeon's left and right eyes are captured by the left eye and right eye tracking units 212a, 212b, respectively, and are processed to obtain the 3D pupillary position data by the processors 214a, 214b and/or the integrator 216.

The measurement process 304 proceeds to process 326 by estimating the pupillary position and corneal reflection data for each of the surgeon's left and right eyes 202a, 202b using the compensation values and/or compensation model determined at process 316. In some embodiments, the captured heard/face motion at step 316 may also be used to compensate the pupil's position and corneal reflection data or the surgeon's 3D gaze point. As described above, the head motion data may be tracked during the calibration process 302 by tracking a head feature using the left eye and right eye tracking units 212a, 212b, and the compensation values and/or compensation model may be used to calculate the change to the pupillary position and/or the corneal reflection data induced by the head motion. The calculated change value may be used to adjust the pupillary position and corneal reflection data for the surgeon's left and right eyes determined at process 324 (e.g. to compensate for the surgeon's head motion). In particular, a function between the head motion and the tracked motions of the eye corners can be formed during the calibration process 302. During the measurement process 304, the motions of the head/eye feature may also be tracked, and the surgeon's head motions may be estimated using the formed function from the calibration process 302. The 3D pupillary position and 3D corneal reflection data may then be converted to the surgeon's 3D gaze point location by the processors 214 by using the gaze point determination model obtained at step 322.

The measurement process 304 proceeds to process 328 by determining the 3D pupillary position and 3D corneal reflection data of each of the surgeon's left and right eyes 202a, 202b. The process for determining the 3D pupillary position and 3D corneal reflection data may be substantially similar to process 318 of method 300 as previously discussed. In some embodiments, the 2D pupillary position and 2D corneal reflection data received from each of the left eye tracking units 212a may be processed by the left eye processor 214a. The pupil's position and corneal reflection of left eye 202a can then be calculated using the relative position between corneal reflection center 365 of the corneal reflection, and the center of the pupil 375 (shown in FIG. 4C). The 3D pupillary position and 3D corneal reflection data of the surgeon's right eye may be determined in a substantially similar manner as the determination of the surgeon's left eye. For example, the 2D pupillary position and 2D corneal reflection data received from each of the right eye tracking units 212b may be processed by the right eye processor 214b. The pupil's position and corneal reflection of right eye 202b can then be calculated using the relative position between corneal reflection center of the right corneal reflection, and the center of the right pupil.

The measurement process 304 proceeds to process 330 by determining the 3D gaze point of the surgeon using the gaze point determination model obtained at process 322 of the calibration process 302. In some embodiments, the 3D pupillary position and 3D corneal reflection data of the surgeon's both eyes determined at process 328 may be processed using the gaze point determination model to determine the 3D location of the surgeon's gaze point. In some examples, the gaze direction vector for each eye can be formed using the determined 3D pupillary position and 3D corneal reflection data of each eye at process 328. The intersection of each gaze direction vector may then be used to determine the surgeon's gaze point.

After the measurement process 304, in some embodiments, the determined 3D gaze point location may be shown onto the image displays 208 shown in FIGS. 3A-3D. The 3D gaze point location may be expressed in any of a variety of suitable representations, such as, without limitation, dots, lines, vectors, arrows, and semi-transparent circles. The gaze point measured by the teleoperational medical system 10 as discussed above may be used in various applications, including both real-time medical procedures and virtual training procedures.

In an exemplary aspect, an first eye tracking system comprises an image display configured to display an image of a surgical field to a user; a right eye tracker configured to measure data about a first gaze point of a right eye of the user, the right eye tracker including a right stereo imaging device; a left eye tracker configured to measure data about a second gaze point of a left eye of the user, the left eye tracker including a left stereo imaging device; and at least one processor configured to process the data about the first gaze point and the second gaze point to determine a viewing location in the displayed image at which the gaze point of the user is directed. In another exemplary aspect, the right stereo imaging device of the first eye tracking system includes at least two cameras configured to receive light from the right eye and the left stereo imaging device includes at least two cameras configured to receive light from the left eye. In another exemplary aspect, the at least one processor of the first eye tracking system is configured to process the data about the first gaze point and the second gaze point to determine the viewing location based on a constant factor corresponding to a constant interpupillary distance.

In another exemplary aspect, the right eye tracker of the first eye tracking system is configured to detect the 2D corneal reflection data of the right eye, and the left eye tracker is configured to detect the 2D corneal reflection data of the left eye.

In another exemplary aspect, the right eye tracker of the first eye tracking system is configured to detect the 2D pupillary position data of the right eye, and the left eye tracker is configured to detect the 2D pupillary position data of the left eye.

In another exemplary aspect, the right eye tracker and the left eye tracker of the first eye tracking system are configured to track positional data about a fixed reference point corresponding to a head feature of the user.

In another exemplary aspect, the at least one processor of the first eye tracking system is configured to process the data about the first gaze point and the second gaze point and compensate for head motions of the user to determine the viewing location based on the positional data about the fixed reference point.

In another exemplary aspect, the first eye tracking system further includes a right eye light emitter and a left eye light emitter, the right eye light emitter configured to emit light of a first wavelength range to the right eye of the user, and the left eye light emitter configured to emit light of the first wavelength range to the left eye of the user.

In another exemplary aspect, the first eye tracking system further includes an optical assembly positioned between the image display and the eyes of the user, the optical assembly comprising a right eye mirror set and a left eye mirror set arranged to provide optical communication between the eyes of the user, the eye trackers, and the light emitters.

In another exemplary aspect, the right eye mirror set of the first eye tracking system is configured to direct light of a second wavelength range from the image display to the right eye of the user, to direct the light of the first wavelength range from the right eye light emitter to the right eye of the user, and to direct reflected light of the first wavelength range from the right eye of the user to the right eye tracker, and the left eye mirror set is configured to direct light of a second wavelength range from the image display to the left eye of the user, to direct the light of the first wavelength range from the left eye light emitter to the left eye of the user, and to direct reflected light of the first wavelength range from the left eye of the user to the left eye tracker.

In another exemplary aspect, the optical assembly of the first eye tracking system is configured to reflect the light of the second wavelength range from the image display and to transmit the light of the first wavelength range from the light emitters.

In another exemplary aspect, the right eye mirror set of the first eye tracking system includes a right beam splitter configured to reflect light of a second wavelength range from the image display to the right eye of the user, to transmit the light of the first wavelength range from the right eye light emitter to the right eye of the user, and to transmit reflected light of the first wavelength range from the right eye of the user to the right eye tracker, and the left eye mirror set includes a left beam splitter configured to reflect light of a second wavelength range from the image display to the left eye of the user, to transmit the light of the first wavelength range from the left eye light emitter to the left eye of the user, and to transmit reflected light of the first wavelength range from the left eye of the user to the left eye tracker.

In another exemplary aspect, the right eye light emitter and the right eye tracker of the first eye tracking system are disposed between the right beam splitter and the image display, and the left eye light emitter and the left eye tracker are disposed between the left beam splitter and the image display.

In another exemplary aspect, the left eye light emitter and the left eye tracker of the first eye tracking system are disposed lateral to the left beam splitter and in a plane between the image display and the left eye, and the right eye light emitter and the right eye tracker are disposed lateral to the right beam splitter and in a plane between the image display and the right eye.

In an exemplary aspect, a first teleoperational medical system for performing a medical procedure, comprises an eye tracking system that includes an image display configured to display an image of a surgical field to a user; at least one right eye tracker configured to measure data about a first gaze point of a right eye of the user; at least one left eye tracker configured to measure data about a second gaze point of a left eye of the user; and at least one processor configured to process the data about the first gaze point and the second gaze point to determine a viewing location in the displayed image at which the gaze point of the user is directed; and a control unit configured to control at least one function of the teleoperational medical system based upon the determined viewing location.

In another exemplary aspect, the image display of the first teleoperational medical system is a 3D image display configured to display to the user a 3D image of the surgical field.

In another exemplary aspect, the first teleoperational medical system further comprises a surgical instrument, wherein the control unit is configured to control at least one function of the surgical instrument in the surgical field based upon the determined viewing location in the displayed image.

In another exemplary aspect, the image display of the first teleoperational medical system is configured to display to the user an image of a user interface comprising a plurality of functional options.

In another exemplary aspect, the control unit of the first teleoperational medical system is configured to initiate at least one of the plurality of functional options if the determined viewing location matches a position of the at least one functional option in the displayed image of the user interface.

In another exemplary aspect, the at least one processor of the first teleoperational medical system is configured to process the data about the first gaze point and the second gaze point to determine the viewing location based on a constant factor corresponding to a constant interpupillary distance.

In another exemplary aspect, the at least one right eye tracker of the first teleoperational medical system is configured to detect the 2D corneal reflection data of the right eye, and the at least one left eye tracker is configured to detect the 2D corneal reflection data of the left eye.

In another exemplary aspect, the at least one right eye tracker of the first teleoperational medical system is configured to detect the 2D pupillary position data of the right eye, and the at least one left eye tracker is configured to detect the 2D pupillary position data of the left eye.

In another exemplary aspect, the at least one right eye tracker and the at least one left eye tracker of the first teleoperational medical system are configured to track positional data about a fixed reference point corresponding to a head feature of the user.

In another exemplary aspect, the at least one processor of the first teleoperational medical system is configured to process the data about the first gaze point and the second gaze point and compensate for head motions of the user to determine the viewing location based on the positional data about the fixed reference point.

In another exemplary aspect, the first teleoperational medical system further includes a right eye light emitter and a left eye light emitter, the right eye light emitter configured to emit light of a first wavelength range to the right eye of the user, and the left eye light emitter configured to emit light of a first wavelength range to the left eye of the user.

In another exemplary aspect, the first teleoperational medical system further includes an optical assembly positioned between the image display and the eyes of the user, the optical assembly comprising a right eye mirror set and a left eye mirror set arranged to provide optical communication between the eyes of the user, the eye trackers, and the light emitters.

In another exemplary aspect, the right eye mirror set of the first teleoperational medical system is configured to direct light of a second wavelength range from the image display to the right eye of the user, to direct the light of the first wavelength range from the right eye light emitter to the right eye of the user, and to direct reflected light of the first wavelength range from the right eye of the user to the at least one right eye tracker, and the left eye mirror set is configured to direct light of a second wavelength range from the image display to the left eye of the user, to direct the light of the first wavelength range from the left eye light emitter to the left eye of the user, and to direct reflected light of the first wavelength range from the left eye of the user to the at least one left eye tracker.

In another exemplary aspect, the optical assembly of the first teleoperational medical system is configured to reflect the light of the second wavelength range from the image display and to transmit the light of the first wavelength range from the light emitters.

In another exemplary aspect, the right eye mirror set of the first teleoperational medical system includes a right beam splitter configured to reflect light of a second wavelength range from the image display to the right eye of the user, to transmit the light of the first wavelength range from the right eye light emitter to the right eye of the user, and to transmit reflected light of the first wavelength range from the right eye of the user to the at least one right eye tracker, and the left eye mirror set includes a left beam splitter configured to reflect light of a second wavelength range from the image display to the left eye of the user, to transmit the light of the first wavelength range from the left eye light emitter to the left eye of the user, and to transmit reflected light of the first wavelength range from the left eye of the user to the at least one left eye tracker.

In another exemplary aspect, the right eye light emitter and the at least one right eye tracker of the first teleoperational medical system are disposed in front of the image display and between the right beam splitter and the image display, and the left eye light emitter and the at least one left eye tracker are disposed in front of the image display and between the left beam splitter and the image display.

In another exemplary aspect, the left eye light emitter and the at least one left eye tracker of the first teleoperational medical system are disposed lateral to the left beam splitter and in front of the image display, and the right eye light emitter and the at least one right eye tracker are disposed lateral to the right beam splitter and in front of the image display.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein.

What is claimed is:

1. A teleoperational medical system for performing a medical procedure, comprising:
    an eye tracking system including:
        an image display comprising a first coordinate frame configured to display an image of a surgical field comprising a second coordinate frame to a user, wherein the user is in a third coordinate frame;
        at least one right eye tracker configured to measure data about a first gaze point of a right eye of the user;
        at least one left eye tracker configured to measure data about a second gaze point of a left eye of the user; and
        at least one processor configured to process the data about the first gaze point and the second gaze point to determine a viewing location in the displayed image at which the first gaze point and the second gaze point of the user are directed; and
    a control unit configured to control at least one function of the teleoperational medical system based upon the determined viewing location.

2. The teleoperational medical system of claim 1, wherein the image display is a 3D image display configured to display to the user a 3D image of the surgical field.

3. The teleoperational medical system of claim 1, further comprising a surgical instrument, wherein the control unit is configured to control at least one function of the surgical instrument in the surgical field based upon the determined viewing location in the displayed image.

4. The teleoperational medical system of claim 1, wherein the image display is configured to display to the user an image of a user interface comprising a plurality of functional options.

5. The teleoperational medical system of claim 4, wherein the control unit is configured to initiate at least one of the plurality of functional options if the determined viewing location matches a position of the at least one of the plurality of functional options in the displayed image of the user interface.

6. The teleoperational medical system of claim 1, wherein the at least one processor is configured to process the data about the first gaze point and the second gaze point to determine the viewing location based on a constant factor corresponding to a constant interpupillary distance.

7. The teleoperational medical system of claim 1, wherein the at least one right eye tracker is configured to detect 2D corneal reflection data of the right eye, and the at least one left eye tracker is configured to detect 2D corneal reflection data of the left eye.

8. The teleoperational medical system of claim 1, wherein the at least one right eye tracker is configured to detect 2D pupillary position data of the right eye, and the at least one left eye tracker is configured to detect 2D pupillary position data of the left eye.

9. The teleoperational medical system of claim 1, wherein the at least one right eye tracker and the at least one left eye tracker is configured to track positional data about a fixed reference point corresponding to a head feature of the user.

10. The teleoperational medical system of claim 9, wherein the at least one processor is configured to process the data about the first gaze point and the second gaze point and compensate for head motions of the user to determine the viewing location based on the positional data about the fixed reference point.

11. The teleoperational medical system of claim 1, further including a right eye light emitter and a left eye light emitter, the right eye light emitter configured to emit light of a first wavelength range to the right eye of the user, and the left eye light emitter configured to emit light of a first wavelength range to the left eye of the user.

12. The teleoperational medical system of claim 11, further including an optical assembly positioned between the image display and the eyes of the user, the optical assembly comprising a right eye mirror set and a left eye mirror set arranged to provide optical communication between at least one of the eyes of the user, at least one of the eye trackers, and at least one of the light emitters.

13. The teleoperational medical system of claim 12, wherein the right eye mirror set is configured to direct light of a second wavelength range from the image display to the right eye of the user, to direct the light of the first wavelength range from the right eye light emitter to the right eye of the user, and to direct reflected light of the first wavelength range from the right eye of the user to the at least one right eye tracker, and the left eye mirror set is configured to direct light of a second wavelength range from the image display to the left eye of the user, to direct the light of the first wavelength range from the left eye light emitter to the left eye of the user, and to direct reflected light of the first wavelength range from the left eye of the user to the at least one left eye tracker.

14. The teleoperational medical system of claim 13, wherein the optical assembly is configured to reflect the light of the second wavelength range from the image display and to transmit the light of the first wavelength range from the light emitters.

15. The teleoperational medical system of claim 13, wherein the right eye mirror set includes a right beamsplitter configured to reflect light of a second wavelength range from the image display to the right eye of the user, to transmit the light of the first wavelength range from the right eye light emitter to the right eye of the user, and to transmit reflected light of the first wavelength range from the right eye of the user to the at least one right eye tracker, and the left eye mirror set includes a left beamsplitter configured to reflect light of a second wavelength range from the image display to the left eye of the user, to transmit the light of the first wavelength range from the left eye light emitter to the left eye of the user, and to transmit reflected light of the first wavelength range from the left eye of the user to the at least one left eye tracker.

16. The eye tracking system of claim 15, wherein the right eye light emitter and the at least one right eye tracker is disposed in front of the image display and between the right beamsplitter and the image display, and the left eye light emitter and the at least one left eye tracker are disposed in front of the image display and between the left beamsplitter and the image display.

17. The eye tracking system of claim 15, wherein the left eye light emitter and the at least one left eye tracker are disposed lateral to the left beamsplitter and in front of the image display, and the right eye light emitter and the at least one right eye tracker are disposed lateral to the right beam-splitter and in front of the image display.

\* \* \* \* \*